US012582715B1

(12) United States Patent　　　(10) Patent No.:　US 12,582,715 B1
　　Ekpenyong et al.　　　　　　　(45) Date of Patent:　　Mar. 24, 2026

(54) CANCER RADIATION THERAPY WITH BIOCOMPATIBLE QUANTUM DOTS FOR SIMULTANEOUS DOSE ENHANCEMENT AND COUNTER-METASTASIS

(71) Applicant: Creighton University, Omaha, NE (US)

(72) Inventors: Andrew Edet Ekpenyong, Omaha, NE (US); Caleb Thiegs, White Bear Lake, MN (US); Anne Hubbard, Terre Haute, IN (US); Yohan Walter, Kaneohe, HI (US); Harrison Kramer, Phoenix, AZ (US); Kimal Honour Djam, Southfield, MI (US)

(73) Assignee: Creighton University, Omaha, NE (US)

( * ) Notice: Subject to any disclaimer, the term of this patent is extended or adjusted under 35 U.S.C. 154(b) by 732 days.

(21) Appl. No.: 17/970,720

(22) Filed: Oct. 21, 2022

Related U.S. Application Data

(60) Provisional application No. 63/270,375, filed on Oct. 21, 2021.

(51) Int. Cl.
　　*A61K 33/04*　　　(2006.01)
　　*A61K 33/44*　　　(2006.01)
　　*A61K 41/00*　　　(2020.01)
　　*A61N 5/10*　　　(2006.01)
(52) U.S. Cl.
　　CPC .......... *A61K 41/0038* (2013.01); *A61K 33/04* (2013.01); *A61K 33/44* (2013.01); *A61N 5/10* (2013.01); *A61N 2005/1021* (2013.01); *A61N 2005/1085* (2013.01)

(58) Field of Classification Search
　　CPC .... A61K 33/04; A61K 33/44; A61K 41/0038; A61N 5/10; A61N 2005/1021; A61N 2005/1085
　　See application file for complete search history.

(56) References Cited

U.S. PATENT DOCUMENTS

2017/0252466 A1 *　9/2017　Peyman ................. A61K 47/68

OTHER PUBLICATIONS

Ruan et al., ACS Applied Materials & Interfaces 2018, 10, 14342-14355 (2018).*
Lee et al., Journal of Biophotonics 2019; 12:e201800172, pp. 1-9 (2019).*

* cited by examiner

*Primary Examiner* — John Kim
(74) *Attorney, Agent, or Firm* — Daniel J. Honz; Advent, LLP

(57) ABSTRACT

Systems and methods for radiation therapy for cancerous tumors using biocompatible quantum dots to provide radiation dose enhancement and resistance to metastasis are described. In an aspect, a method for radiation therapy treatment of cancer cells, includes, but is not limited to, preparing a radiosensitizer fluid, the radiosensitizer fluid including a plurality of biocompatible quantum dots; introducing the radiosensitizer fluid to cancer cells; and irradiating the cancer cells with the radiosensitizer fluid to promote generation of reactive oxygen species and inhibit radiation-induced enhancement of cell-migration.

20 Claims, 13 Drawing Sheets

1

CANCER RADIATION THERAPY WITH BIOCOMPATIBLE QUANTUM DOTS FOR SIMULTANEOUS DOSE ENHANCEMENT AND COUNTER-METASTASIS

CROSS-REFERENCE TO RELATED APPLICATIONS

The present application claims the benefit under 35 U.S.C. § 119(e) of U.S. Provisional Application Ser. No. 63/270,375, filed Oct. 21, 2021, and titled "METHODS FOR SIMULTANEOUS DOSE ENHANCEMENT AND COUNTER-METASTASIS IN CANCER RADIATION THERAPY." U.S. Provisional Application Ser. No. 63/270, 375 is herein incorporated by reference in its entirety.

BACKGROUND

Radiation therapy (RT) is an interdisciplinary and multi-disciplinary endeavor used as a major component in many cancer treatments. Around half of new cancer patients receive radiation therapy as part of their treatment. In spite of billions of dollars spent and decades of research done, cancer remains a leading public health concern worldwide, with millions of new annual cancer cases and millions of deaths resulting therefrom expected in the next two decades. There is still no cure that works for all kinds of cancers. While radiation therapy is a tool for treatment for various cancer types, certain tumors are highly radioresistant and exposure to radiation for certain types of tumors can nega-tively affect metastasis.

SUMMARY

Systems and methods for radiation therapy for cancerous tumors using biocompatible quantum dots to provide radia-tion dose enhancement and resistance to metastasis are described. In aspects, the methods described herein simul-taneously enhance the dose delivered to cancer cells and reduce the metastatic competence (ability to spread and form secondary tumors) of the cells by reducing their migration. The methods described herein can utilize biocompatible quantum dots to promote generation of reactive oxygen species and dose enhancement, while making cells more susceptible to the killing effect of the ionizing radiation, and while reducing metastatic competence of the cells.

In an aspect, a method for radiation therapy treatment of cancer cells, includes, but is not limited to, preparing a radiosensitizer fluid, the radiosensitizer fluid including a plurality of biocompatible quantum dots; introducing the radiosensitizer fluid to cancer cells; and irradiating the cancer cells with the radiosensitizer fluid to promote gen-eration of reactive oxygen species and inhibit radiation-induced enhancement of cell-migration.

In an aspect, a method for radiation therapy treatment of cancer cells, includes, but is not limited to, preparing a radiosensitizer fluid, the radiosensitizer fluid including a plurality of biocompatible quantum dots present in an amount of at least 0.2 micromolar; introducing the radio-sensitizer fluid to human cancer cells; and irradiating the human cancer cells with the radiosensitizer fluid to promote generation of reactive oxygen species and inhibit radiation-induced enhancement of cell-migration.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

BRIEF DESCRIPTION OF DRAWINGS

The Detailed Description is described with reference to the accompanying figures. In the figures, the use of the same reference numbers in different instances in the description and the figures may indicate similar or identical items.

DETAILED DESCRIPTION

Overview

Figure 1:
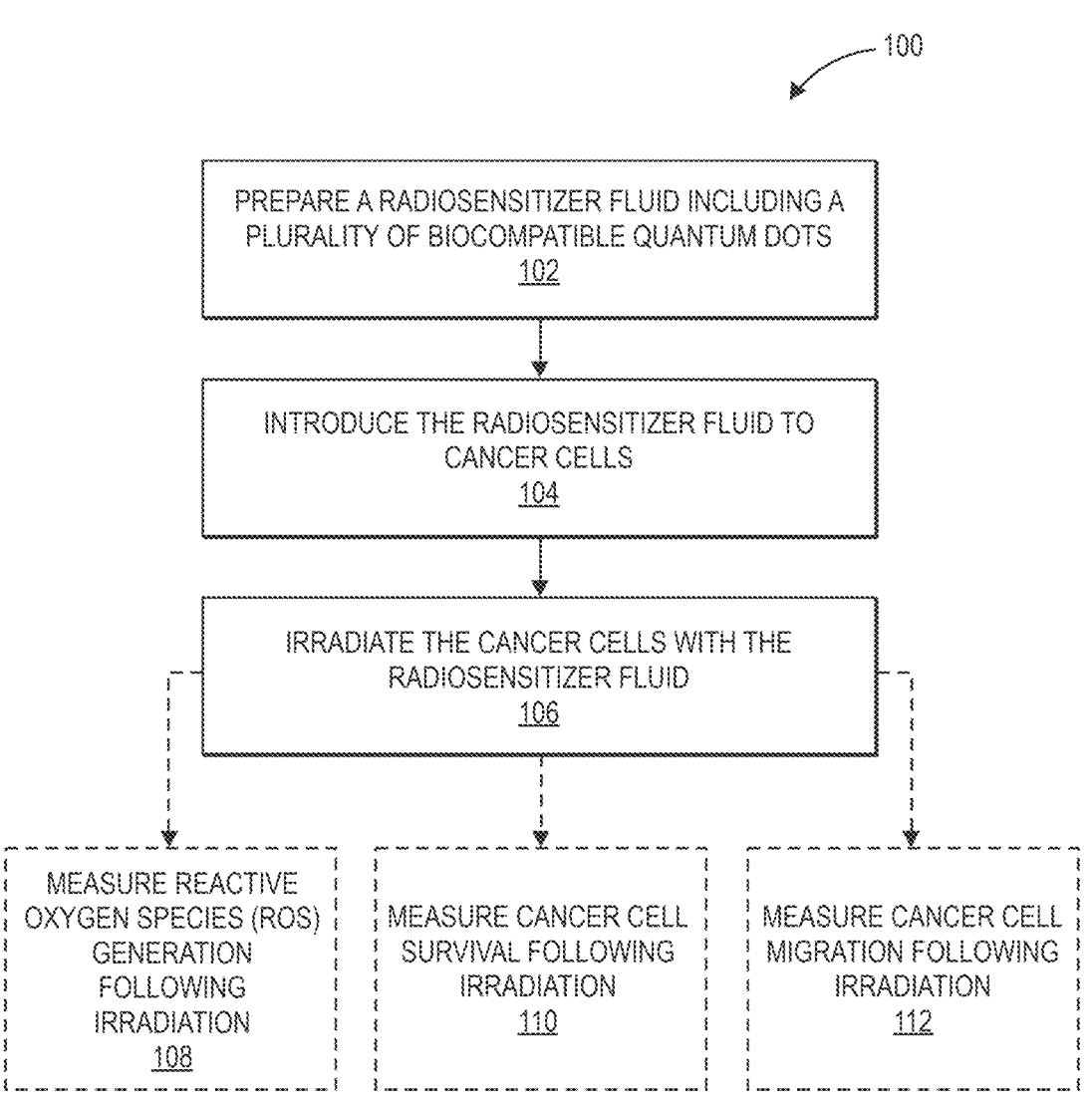
FIG. 1 is a flowchart of a method for radiation therapy for cancerous cells or tumors using biocompatible quantum dots (QD) to provide radiation dose enhancement and resistance to metastasis in accordance with an example implementation of the present disclosure.

Radiation therapy is a tool used in the healthcare field to subject cancerous cells or tumors to high doses of radiation to kill cancer cells and shrink tumors. For certain cancer cells or tumors, the high radiation doses damage cell DNA to prevent cell division or to outright kill the cell. The goal for radiation therapy is to be curative and, in some cases, to be palliative (e.g., via shrinking tumor sizes). However, the efficacy of radiation therapy can be limited by radioresistant cells and by metastasis occurring in many cases despite application of radiation therapy. Metastasis is a multistep process that results with malignancies at secondary sites distant from the primary cancer and accounts for over 90% of cancer related morbidity and mortality. A fundamental component of this process is cell motility or migration of cells from one site to another that traditional radiation therapy may not inhibit, or in certain circumstances, can actually assist with cell migration.

Cell Radioresistance

Highly radioresistant tumors such as brain cancers reduce the efficacy and applicability of radiation therapy. For example, in the case of glioblastoma (GBM), less than 5% patients survive (for 5 years) following diagnosis despite the current standard of care which incorporates initial surgical resection or biopsy and adjuvant postoperative radiation therapy and adjuvant chemotherapy (e.g., Temozolomide). After maximal surgical resection of GBM, the incidence of recurrence at the primary tumor site is greater than 80%, and the median patient survival is about 12 to 18 months. A type of radiation therapy called nanoparticle-mediated radiation therapy (NPRT) aims to enhance therapeutic effects of ionizing radiation through local tumor dose enhancement and radiosensitization, such as through the controlled release of secondary electrons which amplify the generation of reactive oxygen species (ROS) that damage intracellular targets, such as DNA, within their immediate vicinity. However, conventional radiosensitizers can have issues that decrease clinical feasibility, such as due to cytotoxicity of many structures.

Radiosensitizers can be categorized into three groups, specifically, macromolecules, small molecule chemicals, and nanostructures. One example radiosensitizer is a first generation photosensitizer called Photofrin. While Photofrin has shown limited clinical functionality, it has been shown to have poor absorption at therapeutic energies. Nanostructure materials with high atomic number, Z, have been studied to determine functionality as radiosensitizers (e.g., to enhance the dose from ionizing radiation) following a study which showed iodine to radiosensitize cultured mammalian cells to X-rays. Gold nanoparticles have been a focus of research over the past decade. Monte Carlo simulations using gold nanoparticles following ionizing radiation have been shown to increase free radical production. However, application of gold nanoparticles in cancer therapies have been limited due to concerns over selectable biodistribution, pharmacokinetics, and toxicity. In general, clinical feasibility of nanoparticles as radiosensitizers has been diminished due to cytotoxicity of many nanoparticles.

Cell Migration

Use of ionizing radiation as a cancer therapy has shown limitations for various cancers based on influencing migration of the cancer cells. For instance, ionizing radiation can increase the migration of cancer cells before killing the cells, where migration is a key step in metastasis. Unfortunately, such increased migration, prior to cell killing, can promote metastasis if those very cells that escape the cell killing process are cancer stem cells or tumor-initiating cells. Metastasis accounts for over 90% of cancer-related morbidity and mortality. Metastasis is a multistep process that results with malignancies at secondary sites distant from the primary cancer. Research over glioblastoma cell migration has not revealed any effective treatments and research into the effects of ionizing radiation and cellular motility is inconsistent, with both increased and reduced migratory patterns following irradiation being proposed. Currently, radiation-induced enhancement of migration is more often understood than reduction in migration. Dose dependent enhancement of migration in both cancer and non-cancer cells has been shown, with no readily available research on any therapeutic strategies offered to reverse radiation-induced enhancement of migration, where migration is a key step in local tumor invasion and distant metastasis.

Accordingly, the present disclosure is directed, at least in part, to systems and methods for radiation therapy for cancerous tumors using biocompatible radiosensitizers to provide radiation dose enhancement and resistance to metastasis. The present disclosure utilizes biocompatible nanoparticle-mediated radiation therapy (NPRT) to effect both the increased release of electrons that promote reactive oxygen species (ROS) generation and dose enhancement, while making the cells more susceptible to the killing effect of the ionizing radiation, and while limiting cancer cell migration. The NPRT methods described herein can be utilized to treat a variety of cancer and tumor types, including but not limited to, cancers that exhibit inherent radioresistance (e.g., brain cancers, etc.) and cancers that exhibit acquired radioresistance (e.g., pancreatic cancers, etc.). In various aspects, the biocompatible radiosensitizers include biocompatible quantum dots, which can include, but are not limited to, graphene quantum dots, carbon quantum dots, and functionalized core-shell quantum dots (e.g., Cd/Se/ZnS quantum dots).

Multiple types of biocompatible quantum dots were determined to provide (i) quantitative measurement of the ROS produced, (ii) real-time monitoring of cell survival following irradiation, and (iii) real-time quantification of cell migration to confirm anti-metastasis effect. The present disclosure thus provides systems and methods for radiation therapy which (a) enhance localized radiation dose delivery, (b) increase sensitivity of cancer cells to radiation, and (c) eliminate radiation-induced enhancement of cell migration. Furthermore, the present disclosure provides for (d) measuring and monitoring these three effects in view of clinical applications that can be tailored to individual patients in the context of personalized medicine.

Example implementations are described herein utilizing biocompatible quantum dots for the treatment of glioblastoma cell lines. Following irradiation with a compact cell irradiator (e.g., a Faxitron irradiator), enhanced ROS generation was measured via nanoparticle spectroscopy. Additionally, dose enhancement effect and radiosensitization were monitored and quantified using survival curves from real time clonogenic assays (e.g., via a CytoSmart Omni live-cell imager). The anti-migration or counter-metastasis effect was monitored and quantified using an electric cell impedance sensing (ECIS) device. Irradiated glioblastoma cell lines attached and migrated significantly more than non-irradiated cells. Cells treated with graphene quantum dots (GQD) showed radiosensitization and counter-metastatic properties through significantly decreased migration at multiple doses of radiation absorption. The calculated dose enhancement factor (DEF) for ECIS measurements were $1.5\pm0.2$ and $1.4\pm0.1$ for 5 Gy and 20 Gy respectively. This was consistent with cell survival curve DEF calculation of $2.01\pm0.03$ to confirm biocompatible quantum dots as effective radiosensitizers and was further supported by relative peak fluorescence intensity (RPFI) ratio determinations of the glioblastoma cell lines. An example implementation of the treatment of leukemia cell lines is also provided.

Example Implementations

Referring to FIG. 1, a method for radiation therapy for cancerous cells or tumors using biocompatible quantum dots to provide radiation dose enhancement and resistance to metastasis ("method 100") is shown in accordance with example implementations of the present disclosure. The method 100 generally includes preparing a radiosensitizer fluid including a plurality of biocompatible quantum dots 102, introducing the radiosensitizer fluid to cancer cells 104, and irradiating the cancer cells with the radiosensitizer fluid 106 to promote generation of reactive oxygen species and inhibit radiation-induced enhancement of cell-migration. In implementations, the method 100 can include one or more of measuring reactive oxygen species (ROS) generation following irradiation 108, measuring cancer cell survival following irradiation 110, and measuring cancer cell migration following irradiation 112.

The biocompatible quantum dots included in the radiosensitizer fluid can include, but are not limited to, graphene quantum dots, carbon quantum dots, functionalized core/shell quantum dots, and combinations thereof. For example, a functionalized core/shell quantum dot includes a PEGylated ZnS shell with a CdSe core. The quantum dots are semiconducting particles with nanometer-scale sizes (e.g., ranging from about 1 nm to about 20 nm) and can also be referred to as nanoparticles. The quantum dots have unique tunable optical and electronic properties such as high fluorescence quantum yield, resistance to photobleaching, and size and compositional dependent optical properties. Moreover, quantum dots have remarkable resistance to photodegradation and chemical degradation compared to organic fluorophores.

Quantum dots are composed of hundreds to thousands of atoms with electrons expressing a quantum confinement effect. This results in electrons being restricted quantum-mechanically to a small volume, thereby increasing the electron density. This increase in electron density improves the probability of interaction with incident photons. Additionally, the quantum confinement effect increases the energy between the valence and conduction bands known as the semiconductor band gap. This raises the energy required to excite and ionize the atoms making them more suitable for incident photons of higher energies. In implementations, the quantum dots function as fluorescent probes for reactive oxygen species (ROS), a group of important products of hydrolysis leveraged in cancer therapies. Example experimental results of quantification of ROS generation is described further herein.

The quantum dots utilized in the radiosensitizer fluid can include functionalized quantum dots, which can selectively target cancer cells upon application of the radiosensitizer fluid. In implementations, functionalization is achieved through covalently bonding the quantum dots to one or more peptides, antibodies, nucleic acids, ligands, and combinations thereof. For example, the quantum dots can include PEGylated (e.g., attachment to polyethylene glycol) cadmium selenide zinc sulfide (CdSe/ZnS) core-shell quantum dots. In implementations, the quantum dots can be coupled with cell-penetrating peptides to functionalize the quantum dots to cross the lipid bilayer of the cell for intracellular delivery via receptor-mediated or nonspecific endocytosis.

Selectivity for rapidly dividing malignant cells is important for targeting diseased tissues and sparing healthy tissues. Selected ligands with high affinity for certain receptors with an overexpression characteristic to many cancer cells can facilitate increased uptake and retention of quantum dots. As an example, the folate receptor is overexpressed over a large range of human cancers which can be leveraged for internalization of quantum dots both in vitro and in vivo. Coupling quantum dots to certain molecules not only allows for selectivity and intracellular uptake in malignant cells, but also targeting of specific organelles within the cell. For enhancing therapeutic outcomes in radiation therapy, this can provide increased ROS generation which can be focused within closer proximity to intracellular targets like DNA and mitochondria. This enhances the probability of DNA damage and double strand breaks that neutralize malignant cells.

The radiosensitizer fluid can include a pharmaceutically acceptable carrier to facilitate delivery of the radiosensitizer fluid and corresponding biocompatible quantum dots to one or more regions of an individual subject containing the target cancer cells. For example, the pharmaceutically acceptable carrier is suitable for administration via at least one mode of administration via injection, aerosol administration, administration via inhalation, oral administration, systemic IV application, ocular administration, and rectal administration. In implementations, at least a portion of the biocompatible quantum dots are suspended in an aqueous medium.

In some embodiments, the radiosensitizer fluid described herein is adapted for aerosolized uptake (inhalation that goes from nose to brain), intravenous injection as well topical application. Such compositions can include the biocompatible quantum dots conjugated together with a carrier to facilitate inhalation, intravenous injection or topical application. Such a composition may be, for example, in the form of aerosols, solutions, suspensions, emulsions, lotions, creams, microemulsions, nanoemulsions, emulgels, gels, and the like. Compositions described herein may also extend to patches and plasters for application to skin and incorporating biocompatible quantum dots in a form such that it will be released into the skin.

In embodiments, the radiosensitizer fluid can include one or more additional ingredients including, but not limited to, pharmaceutical filler ingredients.

In some embodiments, the radiosensitizer fluid described herein include pharmaceutically and/or dermatologically acceptable excipients including, but not limited to, one or more of carriers, emulsifiers, coemulsifiers, permeation or penetration enhancers, solvents, co-solvents, emollients, antioxidants, preservatives, buffering agents, gelling or thickening agents, polymers, surfactants, soothing agents, pH modifiers, solubilizers, humectants, emollients, moisturizers, oily bases, and the like.

The term "carrier" or "vehicle" denotes organic or inorganic ingredients, natural or synthetic, with which an active ingredient is combined to facilitate application of a composition. Examples of carriers include, but not limited to, water, acetone, alone or in combination with materials such as silicone fluids. In certain embodiments, the carrier can comprise, in addition to water, water-immiscible substances such as any pharmaceutically acceptable fatty esters of natural fatty acids, triglycerides of animal or vegetable, medium chain triglycerides, mixtures of mono-, di- and/or triglycerides, waxes, hydrogenated vegetable oils, and mixtures thereof.

Examples of emulsifiers include, but not limited to, disodium cocoampho diacetate, oxyethylenated glyceryl cocoate (7 EO), PEG-20 hexadecenyl succinate, PEG-15 stearyl ether, ricinoleic monoethanolamide monosulfosuccinate salts, oxyethylenated hydrogenated ricinoleic triglyceride containing 60 ethylene oxide units such as the products marketed by BASF under the trademarks CREMOPHOR® RH 60 or CREMOPHOr® RH 40 (polyoxyl 40 hydrogenated castor oil), polymers such as poloxamers, which are block copolymers of ethylene oxide and propylene oxide, and the nonsolid fatty substances at room temperature (that is to say, at temperatures ranging from about 20 to 35° C.) such as sesame oil, sweet almond oil, apricot stone oil, sunflower oil, octoxyglyceryl palmitate (or 2-ethylhexyl glyceryl ether palmitate), octoxyglyceryl behenate (or 2-ethylhexyl glyceryl ether behenate), dioctyl adipate, and tartrates of branched dialcohols. Sorbitan fatty acid esters are a series of mixtures of partial esters of sorbitol and its mono- and dianhydrides with fatty acids. Sorbitan esters include products marketed as ARLACEL® 20, ARLACEL 40, ARLACEL 60, ARLACEL 80, ARLACEL83, ARLACEL 85, ARLACEL 987, ARLACEL C, PEG-6 stearate and glycol stearate and PEG-32 stearate (TEFOSE® 63), and PEG-6 stearate and PEG-32 stearate (TEFOSE® 1500), glyceryl stearate and PEG 100 stearate (TEFOSE® 165) and any mixtures thereof. Polyethylene glycol ethers of stearic acid are in another group of emulsifiers that can be used in the emulsions. Examples of polyethylene glycol ethers of stearic acid include, but not limited to, steareth-2, steareth-4, steareth-6, steareth-7, steareth-10, steareth-11, steareth-13, steareth-15, steareth-20, polyethylene glycol ethers of stearyl alcohol (steareth 21), and any mixtures thereof. Other emulsifiers include sodium lauryl sulphate, cetyl trialkyl ammonium bromide, polyoxyethylene sorbitan fatty acid esters, and any mixtures thereof.

Nonionic emulsifiers include those that can be broadly defined as condensation products of long chain alcohols, e.g., C8-30 alcohols, with sugar or starch polymers, i.e., glycosides. Various sugars include, but not limited to, glucose, fructose, mannose, and galactose, and various long chain alcohols include, but are not limited to, decyl alcohol, cetyl alcohol, stearyl alcohol, lauryl alcohol, myristyl alcohol, oleyl alcohol, and any mixtures thereof. Other useful nonionic emulsifiers include condensation products of alkylene oxides with fatty acids such as alkylene oxide esters of fatty acids. Other nonionic surfactants are the condensation products of alkylene oxides with 2 moles of fatty acids such as alkylene oxide diesters of fatty acids.

Emulsifiers can also include any of a wide variety of cationic, anionic, zwitterionic, and amphoteric surfactants that are known in the art. Examples of anionic emulsifiers include, but are not limited to, alkyl isethionates, alkyl and alkyl ether sulfates and salts thereof, alkyl and alkenyl ether phosphates and salts thereof, alkyl methyl taurates, and soaps (e.g., alkali metal salts and sodium or potassium salts) of fatty acids. Examples of amphoteric and zwitterionic emulsifiers include those which are broadly described as derivatives of aliphatic secondary and tertiary amines in which the aliphatic radical can be straight or branched chain, wherein one of the aliphatic substituents contains from about 8 to about 22 carbon atoms and one contains an anionic water solubilizing group, e.g., carboxy, sulfonate, sulfate, phosphate, or phosphonate. Specific examples include, but not limited to, alkylimino acetates, iminodialkanoates and aminoalkanoates, imidazolinium and ammonium derivatives. Other suitable amphoteric and zwitterionic emulsifiers include betaines, sultaines, hydroxysultaines, alkyl sarcosinates, and alkanoyl sarcosinates.

Silicone emulsifiers can include organically modified organopoly siloxanes, sometimes called silicone surfactants. Useful silicone emulsifiers can include dimethicone copolyols. These materials are polydimethyl siloxanes, which have been modified to include polyether side chains such as polyethylene oxide chains, polypropylene oxide chains, mixtures of these chains, and polyether chains containing moieties derived from both ethylene oxide and propylene oxide.

Co-emulsifiers include, but not limited to, polyoxylglycerides such as oleoyl macrogolglycerides (LABRAFIL® M 1944CS), linoleoyl macrogolglycerides (LABRAFIL® M 2125CS), caprylocaproyl macrogolglycerides (LABRASOL®), cetyl alcohol (and) ceteth-20 (and) steareth-20 (EMULCIRE™ 61 WL 2659), glyceryl stearate (and) PEG-75 stearate (GELOT® 64), d-alpha tocopheryl polyethylene glycol 1000 succinate (TPGS) and any mixtures thereof.

The term "solvent" refers to components that aid in the dissolution of one or more portions of the radiosensitizer fluid. Solvents serve to maintain a solution of one or more portions of the radiosensitizer fluid (e.g., one or more biocompatible quantum dots) in the radiosensitizer fluid. Some solvents can also enhance percutaneous penetration and/or act as humectants. Solvents that can be used in the present radiosensitizer fluid can include water-immiscible substances such as fatty esters of natural fatty acids, triglycerides of animal or vegetable, medium chain triglycerides, mixtures of mono-, di- and/or triglycerides, waxes, hydrogenated vegetable oils, and mixtures thereof. Some specific examples include, but not limited to, castor oil, isopropyl myristate, dimethyl isosorbide, oleyl alcohol, labrafil, labrasol, medium chain triglyceride, diethyl sebacate, lanolin oil, citrate triisocetyl triglycerides having 10-18 carbon atoms, caprylic/capric triglycerides, coconut oil, corn oil, cottonseed oil, linseed oil, oil of mink, olive oil, palm oil, sunflower oil, nut oil, saturated paraffin oils, mineral oils, vegetable oils or glycerides, and the like. The solvent can also be selected from the group comprising monoalkyl ether of diethylene glycol such as diethylene glycol monomethyl ether, diethylene glycol monoethyl ether or mixtures thereof.

The term "emollients" refers to substances that soften and soothe the skin. They can be used to prevent dryness and scaling of the skin. Examples of emollients that can be used in the present radiosensitizer fluid include, but not limited to, oils of natural origin such as almond oil, coconut oil, olive oil, palm oil, peanut oil and the like, fatty acids such as lauric acid, myristic acid, palmitic acid, and stearic acid, monohydric alcohol esters of the fatty acids such as ethyl laurate, isopropyl laurate, ethyl myristate, n-propyl myristate, isopropyl myristate, ethyl palmitate, isopropyl palmitate, methyl palmitate, methyl stearate, ethyl stearate, isopropyl stearate, butyl stearate, isobutyl stearate, amyl stearate, and isoamyl stearate, glycols such as ethylene glycol, diethylene glycol, polyethylene glycol, branched aliphatic alcohols such as lauryl alcohol, myristyl alcohol, and stearyl alcohol, or mixtures thereof. Exemplary emollients include caprylic/capric triglyerides, castor oil, ceteareth-20, ceteareth-30, cetearyl alcohol, ceteth 20, cetostearyl alcohol, cetyl alcohol, cetyl stearyl alcohol, cocoa butter, diisopropyl adipate, glycerin, gyceryl monooleate, glyceryl monostearate, glyceryl stearate, isopropyl myristate, isopropyl palmitate, lanolin, lanolin alcohol, hydrogenated lanolin, liquid paraffins, linoleic acid, mineral oil, oleic acid, white petrolatum, polyethylene glycol, polyoxyethylene glycol fatty alcohol ethers, silicones and mixtures thereof.

Silicones are typically organically modified organopoly siloxanes, sometimes called silicone surfactants. Useful polysiloxane or silicone emollients include, but not limited to, polysiloxane polymer, dimethicone copolyols, cyclomethicones. These materials are polydimethyl siloxanes, which have been modified to include polyether side chains such as polyethylene oxide chains, polypropylene oxide chains, mixtures of these chains, and polyether chains containing moieties derived from both ethylene oxide and propylene oxide.

The term "antioxidants" are substances which inhibit oxidation or suppress reactions promoted by oxygen or peroxides. Antioxidants, especially lipid-soluble antioxidants, can be absorbed into the cellular membrane to neutralize oxygen radicals and thereby protect the membrane. In some embodiments, the radiosensitizer fluid includes antioxidants to protect non-cancerous cells from generation of the ROS by the biocompatible quantum dots upon irradiation. The antioxidants can include, but are not limited to, ascorbic acid (vitamin C), glutathione, lipoic acid, uric acid, sorbic acid, carotenes, α-tocopherol (vitamin E), TPGS, ubiquinol, butylated hydroxyanisole, butylated hydroxytoluene, sodium benzoate, propyl gallate (PG, E310), and tertiary-butylhydroquinone.

The term "preservative" refers to a natural or synthetic chemical that prevents the decomposition of the composition by microbial growth or by undesirable chemical changes. Preservatives can be incorporated into the radiosensitizer fluid for protecting against the growth of potentially harmful microorganisms. While microorganisms tend to grow in an aqueous phase, certain microorganisms can also reside in a hydrophobic or oil phase. Examples of preservatives that can be used in the radiosensitizer fluid include, but are not limited to, methylparaben, propylparaben, benzyl alcohol, chlorocresol, benzalkonium chloride, cetrimonium chloride, sodium edetate, boric acid, sorbic acid, or any mixtures thereof.

The term "thickening agents" or "gelling agents" refer to substances that can be used to give bulkiness to the radiosensitizer fluid. Examples of thickening agents or gelling agents that can be used in the radiosensitizer fluid include, but not are limited to: carbomers, polyethylene glycols, acrylate polymers, methacrylate polymers, polyvinylpyrrolidones, copolymers based on butyl methacrylate and methyl methacrylate povidone, vinyl acetates, polyvinyl acetates, celluloses, gums, alginates, cellulose acetate phthalates, cellulose acetate butyrates, hydroxypropyl methyl cellulose phthalates, and the like. Examples include CARBOPOL® products, PEG 400, EUDRAGIT® 100, EUDRAGIT® RSPO, EUDRAGIT® RLPO, EUDRAGIT® ND40, PLASDONE®, copolymers based on butyl methacrylate and methyl methacrylate (PLASTOID® B), alkyl celluloses such as ethyl celluloses and methyl celluloses, hydroxyalkyl celluloses such as hydroxyethyl cellulose and hydroxypropyl cellulose, hydroxyalkyl alkyl celluloses such as hydroxypropyl methyl celluloses and hydroxybutyl methyl celluloses, gums such as xanthan gum, tragacanth, guar gum, locust bean gum, acacia, and the like.

In an embodiment, the thickening agents can include non-polymeric thickening agents, such as fatty alcohols. Examples of fatty alcohols include, but are not limited to: cetyl alcohol, paraffin, stearyl alcohol, white wax, wax cetyl esters, microcrystalline wax, anionic emulsifying wax, nonionic emulsifying wax, yellow wax, castor oil, ceresin, cetostearyl alcohol, cyclomethicone, glyceryl behenate, hectorite, myristyl alcohol, cetylstearyl alcohol, triolein, and lanolin. Other thickening agents or gelling agents or polymers that can be utilized in the present radiosensitizer fluid include, but are not limited to, polyamides, polycarbonates, polyalkylenes, polyalkylene glycols, polyalkylene oxides, polyalkylene terepthalates, polyvinyl alcohols, polyvinyl ethers, polyvinyl esters, polyvinyl halides, polyglycolides, polysiloxanes, polyurethanes and copolymers thereof, cellulose ethers, cellulose esters, nitrocelluloses, polymers of acrylic and methacrylic esters, cellulose acetates, cellulose propionates, cellulose acetate butyrates, cellulose acetate phthalates, carboxylethyl celluloses, cellulose triacetates, cellulose sulphate sodium salts, poly(methyl ethacrylate), poly(ethylmethacrylate), poly(butylmethacrylate), poly (isobutylmethacrylate), poly(hexylmethacrylate), poly(isodecylmethacrylate), poly(lauryl methacrylate), poly(phenyl methacrylate), poly(methyl acrylate), poly(isopropyl acrylate), poly(isobutyl acrylate), poly(octadecyl acrylate), polyethylenes, polypropylenes, poly(ethylene glycol), poly(ethylene oxide), poly(ethylene terephthalate), poly(vinyl alcohol), poly(vinyl acetate), poly(vinyl chloride), polystyrenes, and the like, including their mixtures thereof.

Examples of other polymers that can act as thickening agents or gelling agents include, but not limited to, synthetic polymers, such as polymers of lactic acid and glycolic acid, polyanhydrides, poly(ortho ester), polyurethanes, poly(butyric acid), poly(valeric acid), poly(caprolactone), poly(hydroxybutyrate), poly(lactide-co-glycolide), poly(lactide-co-caprolactone), and natural polymers such as alginate and other polysaccharides that include but not limited to arabinans, fructans, fucans, galactans, galacturonans, glucans, mannans, xylans (such as, for example, inulin), levan, fucoidan, carrageenan, galactocarolose, pectic acid, pectin, amylose, pullulan, glycogen, amylopectin, cellulose, dextran, pustulan, chitin, agarose, keratan, chondroitan, dermatan, hyaluronic acid, alginic acid, xanthan gum, starches, and various other natural homopolymers and heteropolymers, such as those containing one or more of aldoses, ketoses, acids or amines, erythrose, threose, ribose, arabinose, xylose, lyxose, allose, altrose, glucose, mannose, gulose, idose, galactose, talose, erythrulose, ribulose, xylulose, psicose, fructose, sorbose, tagatose, mannitol, sorbitol, lactose, sucrose, trehalose, maltose, cellobiose, glycine, serine, threonine, cysteine, tyrosine, asparagine, glutamine, aspartic acid, glutamic acid, lysine, arginine, histidine, glucuronic acid, gluconic acid, glucaric acid, galacturonic acid, mannuronic acid, glucosamine, galactosamine, and neuraminic acid, and naturally occurring derivatives thereof, and including dextran and cellulose, collagen, albumin and other hydrophilic proteins, zein and other prolamines and hydrophobic proteins, copolymers and mixtures thereof.

It is contemplated that some of the excipient substances described above can have more than one function in a formulation. For example, a substance can be both a solvent and a penetration enhancer, or both a solvent and a carrier. The categorizations of materials described above are not to be construed as limiting or restricting in any manner.

Example implementations, research, and methodologies for preparation, application, and irradiation of the radiosensitizer fluid are provided below.

Radiosensitizer Fluid Implementations and Experimental Procedures

Implementations of the radiosensitizer fluid utilized in method 100 are described herein, with experimental procedures involving three cancer cell lines (one leukemia cell line and two glioblastoma cell lines) and three types of biocompatible quantum dots to measure fluorescence spectrometry, cell survival, and cell migration for different combinations of cell line, quantum dot type, and ionizing radiation doses. The materials and tools are first provided, with experimental procedures provided following.

Biological Materials

Jurkat E6-1 human T cell leukemia cell line (ATCC® TIB-152™) were obtained from American Type Cell Culture Collection (ATCC, Manassas, VA, USA). The cell line cultures in suspension and possesses lymphoblast morphology. Due to higher oxygen tension, these cells are radiosensitive and were chosen as a control to demonstrate outcomes of IR exposure.

U-87 MG human glioblastoma cells (ATCC® HTB-14™) were obtained from American Type Culture Collection (ATCC, Manassas, VA, USA). U-87 MG is a long-standing established cell line derived from a malignant glioma grade IV. These are a hypodiploid human cell line that are adherent with epithelial morphology.

T98-G human glioblastoma cells (ATCC® CRL-1690™) were obtained from American Type Culture Collection (ATCC, Manassas, VA, USA). Derived from a human glioblastoma multiforme tumor, T98-G expresses characteristics of anchorage independence and immortality. These are a hyperpentaploid human cell line that are adherent with fibroblast morphology.

Chemical Materials

Carbon quantum dots suspended in water at concentration ≥2% were obtained from Sigma-Aldrich (Sigma-Aldrich, Saint Louis, MO, USA). Carbon quantum dots (CQDs) have strong fluorescence properties that are tunable allowing for controllable excitation wavelength. Carbon quantum dots absorb wavelengths of 350 nm with a fluorescent emission wavelength of 450-550 nm and quantum efficiency ≥5%.

Graphene quantum dots aqua green luminescent suspended in water at concentration of 1 mg/mL were obtained from Sigma-Aldrich (Sigma-Aldrich, Saint Louis, MO, USA). Graphene quantum dots (GQDs) possess tunable fluorescence properties. GQD have a small diameter of <5 nm with an excitation wavelength of 485 nm and 530±10 nm emission. The full width half maximum is 80 nm with a quantum yield ≥17% as per manufacturer's specifications.

CdSe/ZnS core-shell quantum dots suspended in water at concentration of 4 M were obtained from Sigma-Aldrich (Sigma-Aldrich, Saint Louis, MO, USA). The CdSe/ZnS core-shell quantum dots are functionalized through PEGylation, which is the process of attaching polyethylene glycol to facilitate making the quantum dot hydrophilic and biocompatible. As per the manufacturer's specifications, the fluorescence emission wavelength is 540±10 nm with quantum yield >50%.

Radiation Equipment and Methods

Cells were irradiated in lab via Faxitron CellRad, a compact X-ray system. The tube potential can be manually set between 10 and 130 kVp with tube current ranging from 0.1 mA to 5 mA. Cells are placed at the center of the turntable platform at the central axis of the X-ray beam to ensure uniform dose delivery. The beam has improved uniformity at the center away from the edges. The field size of the beam can be adjusted from 9 to 27 cm in diameter. The unit is coupled with an integrating ionization chamber-based dosimeter housed beneath the turntable. This allows for the convenient Auto-Dose Control feature that permits accurate dose delivery with manual setting of the tube potential and current. Irradiation was performed with 26.8 cm field size at 100.0 kVp tube potential and 5.0 mA current. The large field size was chosen to provide a uniform beam profile where specimens were placed. The CellRad system was warmed up prior to every irradiation including an automated dose quality assurance. Specimens were placed on shelves within the unit.

Clinical energy level irradiation was performed with a Siemens Oncor clinical LINAC. The unit is composed of an 82-leaf multileaf collimator (MLC) capable of delivering 6 & 15 MV photons. The unit was calibrated with 6 MV 10 cm×10 cm photon beam to 1 cGy/monitor unit (MU) at dmax=1.5 cm. Dose rate was 300 MU/min.

A 3D water phantom and a stepper motor were utilized to hold and place experimental conditions remotely at a desired depth in tissue equivalent water (e.g., a depth of 1.5 cm where 1 MU=1 cGy). A 1.5 ml microtube holder was constructed with Delrin Acetal AF Resin Rod (McMaster- Carr 8579K24) with a density of 1.42 g/cm³ similar to the density of water. The resin is a polyoxymethylene (POM) plastic with an electron per atomic mass of 0.53287 and a mean excitation energy of 77.4 eV that is comparable to water with an electron per atomic mass of 0.55509 and a mean excitation energy of 79.7 eV. The rod was placed on a lathe and dimensions were reduced to resemble that of an ionization chamber for compatibility with the 3D water phantom stepper motor. An automated drill press was used to produce holes to accommodate 1.5 ml microtubes. The microtubes were mounted horizontally within the water phantom for dose uniformity throughout the specimens. The 3D water phantom was placed on the Siemens Oncor couch and filled with room temperature water. Water level and couch height were adjusted until the surface of the water was at 100 cm SSD. The 1.5 ml microtubes containing appropriate conditions to be irradiated were removed from the warming canister and placed horizontally in the holder. The stepper motor was zeroed by disengaging and manually manipulating the motor until the microtubes were at water level. The stepper motor was then reengaged and the cells were remotely at 1.5 cm below the surface of the water or dmax for a 6 MV photon beam. For conditions 6 and 7 (described below), the LINAC was instructed to deliver 500 MU correlating to 5 Gy at 1.5 cm. Similarly, conditions 3, 4, and 8 (described below) received 20 Gy by delivery of 2000 MU.

Fluorescence Equipment and Methods

Fluorescent intensities were measured by an USB650 Spectrometer (Ocean Optics, Winter Park, FL, USA) that was coupled to a custom fabricated 1 cm pathlength cuvette holder. Experimental conditions were excited with a 395 nm to 405 nm UV LED (3.3V, 0.2 Å) light source (RadioShack, Omaha, NE, USA) that was positioned perpendicular to the spectrometer to avoid saturation from the UV LED. The LED light source was powered by an external power supply supplemented with a single external resistor to control current. Spectra of the fluorescent intensity versus wavelength were generated using OceanView 1.6.5 software from signals generated by the USB650 Spectrometer.

Clonogenic Assay Equipment and Methods

Clonogenic assays were performed with automated monitoring via CytoSMART Omni software (CytoSMART™ Technologies B.V., Eindhoven, Netherlands). The system was housed in a humidified $CO_2$ incubator for real-time remote monitoring of live cells. Operating conditions included a temperature of 37° C. and 5% carbon dioxide. The system included an LED light source, 5 MP CMOS camera, and 99 mm×131 mm scanning area. CytoSMART software contains Cloud-based image analysis with cell proliferation, cytotoxicity, migration, and colony detection features.

Electric Cell-Substrate Impedance Sensing Equipment

The Electric Cell-Substrate Impedance Sensing (ECIS) method was employed to quantify the behavior of cells post irradiation. Impedance sensing provides qualitative information about cell-substrate interactions, cell-cell communication, and cell adhesion. The ECIS system is composed of two main units: a Station Controlled Zθ and an Array Station. The Station Controlled Zθ was set up outside the incubator and contained electrical equipment for supplying alternating current signal by an oscillator and taking impedance measurements from the circuits. This was connected to a 16 W Array Station housed within the incubator. The incubator was humidified at 37° C. and 5% $CO_2$. The 16 W Array Station was equipped to accept standard 8 well arrays as well as resistance, impedance, and capacitance measuring electronics. Gold-plated 8W10E+ECIS Well Arrays that contain a total of 40 electrodes were used for all ECIS experiments. A computer was connected to the Station Controller via USB and measurements were compiled by ECIS Software.

Cell Culture Equipment and Methods

Cells were accepted in 1 ml cryovials on dry ice from ATCC. Appropriate medium (DMEM+10% FBS+1% PS for U87/T98G and RPMI+10% FBS+1% PS for Jurkat) was prewarmed in a water bath at 37° C. Cryovials were warmed in a water bath at 37° C. until thawed and immediately transitioned to a sterile fume hood. 9 ml of fresh medium was added to the 1 ml of cells. 90 µL were removed and added to 10 µL of Trypan Blue to determine density and viability using a hemocytometer. The remainder was centrifuged with 37° C. heating at 800 rpm for 5 minutes. Centrifuged medium was removed. Cells were resuspended in appropriate medium and seeded into a T-75 flask to be placed in a sterile humidified incubator.

Subcultures for U-87 MG, T98-G, and Jurkat lines were performed as per ATCC protocol in a humidified incubator at 37° C. and 5% $CO_2$. ATCC formulated Eagle's Minimum Essential Medium (EMEM) supplemented with 10% fetal bovine serum (FBS) was used for U-87 MG and T98-G cell culture. Jurkat cells were subcultured using RPMI-1640 supplemented with 10% fetal bovine serum and 1% penicillin-streptomycin. Cells were cultivated in Thermo Fisher Scientific T-75 Flasks with filtered cap. Cells were removed from culture flasks using 0.25% trypsin with ethylenediaminetetraacetic acid (EDTA). Experiments were performed during the rapidly proliferating logarithmic phase of cell growth with cell density of $1\times10^6$ viable cells/ml. Viability was determined with Trypan Blue obtained from Sigma-Aldrich and manual cell counting using a hemocytometer.

For adherent U87 MG and T98-G, subculturing began with pre warming PBS, EMEM+10% FBS, and 0.25% Trypsin with EDTA in a water bath to 37° C. Cells in T-75 flask were removed from incubator and transitioned to sterile fume hood. The old medium was removed, and cells were rinsed with 10 mL of PBS then removed. 2.5 mL of 0.25% trypsin with EDTA was then added to the cells. The cells were then placed back into the incubator for 5 minutes. Cells were then observed under a microscope to ensure they were all lifted from the bottom of the flask. Once all cells detached, they were placed back inside the sterile fume hood where 5 ml of EMEM+10% FBS was added to neutralize the trypsin. 90 µL of cells were removed and added to 10 µL Trypan Blue to determine cell density and viability with a hemocytometer. The remainder of the cells were centrifuged with 37° C. heating at 800 rpm for 5 minutes. The old medium was then discarded, and cells were resuspended in the appropriate amount of EMEM+10% FBS for subculturing density of $2\times10^5$ viable cells/ml by pipetting until cells were homogenously distributed. 15 mL of cells with density of $2\times10^5$ cells/mL were then seeded into a fresh T-75 and placed in a humidified incubator.

For nonadherent Jurkat cells, subculturing began with pre warming RPMI-1640+10% FBS+1% penicillin-streptomycin to 37° C. in water bath. Cell density and viability were determined by taking 90 µL of cells with 10 µL of Trypan Blue for manual counting in a hemocytometer. Density was reduced to $1\times10^5$ viable cells/mL using fresh medium. Once at this density, 15 mL of cells were placed in T-75 flask with remaining cells discarded.

Cell Preparation and Experimental Conditions

Preparation of the cells for experiments was performed identically to the subculture protocol described above with the exception of a final density of $1\times10^6$ viable cells/mL. This density was used for all experimental conditions, including conditions with cells treated with nanoparticles (NP, e.g., biocompatible quantum dots). Eight conditions were utilized for experiments described herein according to Table 1:

TABLE 1

| Condition | Description |
| --- | --- |
| 1 | Growth Medium |
| 2 | Cells |
| 3 | Cells + 20 Gy |
| 4 | Cells + NPs + 20 Gy |
| 5 | Cells + NPs |
| 6 | Cells + 5 Gy |
| 7 | Cells + NPs + 5 Gy |
| 8 | Cells + NPs + 20 Gy |

The first condition contained only medium to confirm appropriate operation of equipment. For ECIS, this was to show proper electrical connections and function of electrodes that appears as a constant value for impedance throughout data collection. For fluorescence spectroscopy, this was to confirm appropriate recording of the spectrum. This was confirmed when the spectrum showed a single peak at 395-405 nm due to the UV source used for excitation. The second condition contained only cells to compare against the various other conditions in which cells were treated with a combination of nanoparticles (NPs) and radiation. The third condition was cells treated with 20 Gy. This high dose was chosen to simulate typical dose associated with radiation therapy for glioblastoma. The fourth condition was initiation of the nanoparticle radiosensitizer that was then treated with 20 Gy to directly compare nanoparticle effects at clinical doses. The fifth condition consisted of cells and the nanoparticles to evaluate any effect on biocompatibility. The sixth condition contained cells that were treated with 5 Gy to observe behavior at lower doses. The seventh condition was cells treated with nanoparticles and 5 Gy. The eighth condition was cells treated with nanoparticles and 20 Gy, a duplicate of condition 4, and provided another check to ensure consistency in the experiment.

Fluorescence Intensity Analysis

Fluorescence intensity of quantum dots is a technique to quantitatively assess reactive oxygen species in the context of radiation therapy and chemotherapy. Reactive oxygen species cause biological damage and are the basis of radiation therapy treatment of cancers. Therefore, greater quantities of ROS can be associated with increased levels of biological damage. The presence of nanoparticles during irradiation increases the production of ROS through secondary electrons. This technique is employed to simultaneously quantify and enhance ROS generation that in turn radiosensitize the cells due to increased ROS generation and biological damage.

Analysis of the fluorescence spectra was performed using Origin Analysis Software (OriginLab 2021, Northampton, MA, USA). The spectra were averaged over 5 trials of intensity in arbitrary light units (a.u.) vs. wavelength (nm) for each experimental condition. The standard deviation, a, was used to determine the standard error of the mean (SE) given by Equation 1, where N is the number of trials:

$$SE = \left(\frac{\sigma}{\sqrt{N}}\right)$$

(1)

For quantum dots with single emission wavelength of $540\pm10$ nm, the Gaussian fit was employed. Statistical comparison among the different experimental conditions was performed using Analysis of Variance, ANOVA, function in OriginLab 2021.

The effect of the nanoparticles on irradiated cells is quantified by the relative peak fluorescent intensity (RPFI) ratio. This provides the percent change in peak fluorescence intensity used to quantify the effect of cells treated with nanoparticles and radiation compared to radiation alone. The RPFI ratio was calculated through Equation 2 below:

$$RPFI = \left| \frac{I_{Cells+NPs+IR} - I_{Cells}}{I_{Cells+NPs} - I_{Cells+NPs+IR}} \right| \quad (2)$$

Clonogenic Assays for Cell Survival Curves

Cell survival studies are utilized in determining the effectiveness of radiation therapy using clonogenic assays. Survival curves measure the survival fraction (SF) defined by the number of colonies that are formed after treatment. This is performed as a function of dose. This in vitro assessment quantifies effectiveness of radiation on a clonogenic population of cells. Cells that are unable to proliferate and form colonies are effectively sterilized. Surviving cells are defined by their ability to form colonies of at least 50 cells.

Clonogenic assays in the present disclosure consisted of conditions 2 through 8 listed previously in Table 1. These conditions were placed into 48 well plates containing 48 individual wells with working volume from 0.5 mL to 0.8 mL media. 167 cells were seeded into each well with 0.5 mL of appropriate medium. Three-quarters of the medium (375 L) was refreshed every four days. The number of colonies that formed were counted on day 21.

Survival curves were constructed for cells with and without NPs at 0 Gy, 5 Gy, and 20 Gy. This was plotted using Origin software and fit to the linear quadratic model. Here, the effectiveness of nanoparticles was quantified using dose enhancement factor (DEF), which is the ratio of the area under the survival curves with and without nanoparticles shown in Equation 3 below:

$$DEF = \left( \frac{\text{Area Under Survival Curve for Cell Culture without } NPs}{\text{Area Under Survival Curve for Cell Culture with } NPs} \right) \quad (3)$$

Electric Cell-Substrate Impedance Sensing (ECIS) Analysis

Real time assessment of adherence, migration, and proliferation were performed in vitro via an ECIS technique. This provides a noninvasive label-free method of continuous and quantitative monitoring of adherent cells while they are incubated in culture. The ECIS system includes a circuit containing a gold-plated electrode, counter electrode, alternating voltage source, and cell culture substrate. The circuit is completed by the culture medium and adherent cells as they migrate and proliferate across the electrode region. The weak alternating (AC) voltage is applied across the circuit in multiple frequencies ranging between 10 Hz and 100 kHz. The impedance (Z) or effective resistance of the circuit is defined by Equation 4 below, where R is the total resistance, and $X_C$ is the capacitive reactance of the circuit:

$$Z=R^2+X_C{}^2 \quad (4)$$

In implementations, the capacitive reactance is defined by $$X_c = \frac{1}{2\pi f C}.$$

Since the capacitive reactance is inversely proportional to both frequency and capacitance, the impedance can be modulated by the frequency of the AC voltage. At lower frequencies (e.g., ranging from 100 Hz to 2,000 Hz), the capacitive reactance is large and is the dominant contributor to the impedance. The current primarily follows ions in the medium that are situated between, above, and below cells. Therefore, low frequencies provide quantitative measurements of the interactions between cells as well as their adherence to the cell substrate.

At high frequencies (e.g., generally greater than 40,000 Hz), the capacitive reactance is greatly reduced, lowering the impedance. The impedance is dominated by total resistance and current is directed across membranes of cells in the substrate. This scenario facilitates measurements of cell coverage over the electrode quantifying migration, proliferation, and cell death. Similar to the dose enhancement factor (DEF) for clonogenic derived cell survival curves, the dose enhancement factor was calculated by the ratio of the area under the curves with and without nanoparticles represented by Equation 5 below, and was performed over the same period of impedance monitoring and at the same dose:

$$DEF = \frac{\left( \begin{array}{l} \text{Area Under the Normalized Impedance of} \\ \text{Irradiated Cell Culture without } NPs \end{array} \right)}{\left( \begin{array}{l} \text{Area Under the Normalized Impedance of} \\ \text{Irradiated Cell Culture with } NPs \end{array} \right)} \quad (5)$$

Radiosensitizer Fluid Implementation and Experimental Results

PEGylated QD Fluorescence Spectroscopy Concentration Dependency

Spectroscopic experiments with PEGylated QD were performed where the emission wavelength was determined to be 539 nm$\pm$30 nm. This is in excellent agreement of manufacturers specification of 540 nm$\pm$10 nm. This confirms that the photophysical properties of the PEGylated CdSe/ZnS variations in these properties were attributed to the fixed variables of interest in the experimental conditions, particularly the relationship between fluorescence intensity and concentration of QDs.

Figure 2A:
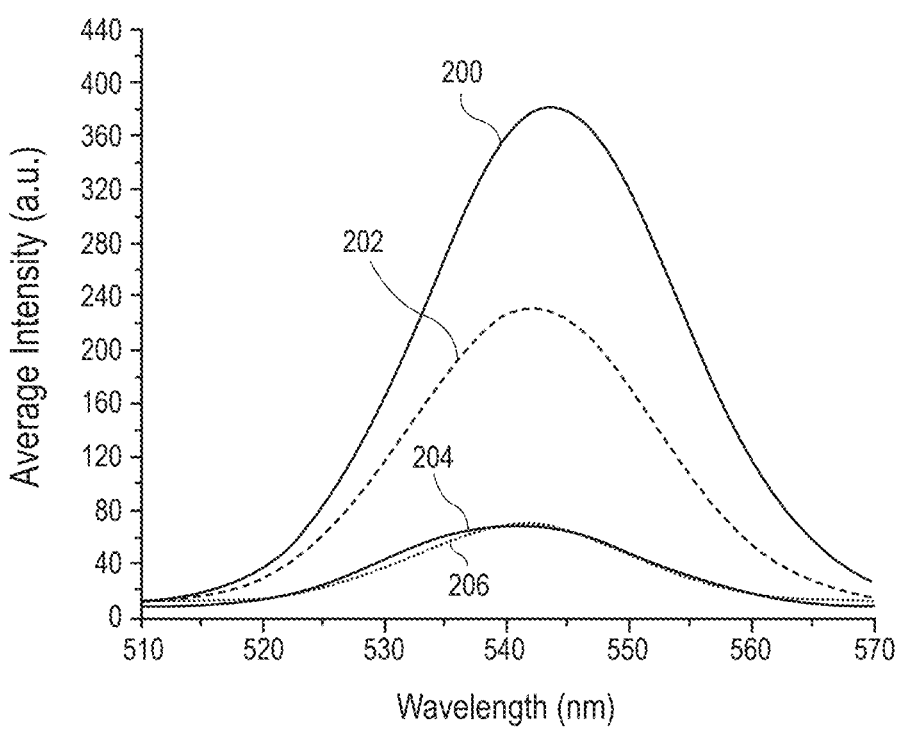
FIG. 2A is a chart of the average fluorescence intensity spectra for a line of glioblastoma cells inoculated with various concentrations of QD and irradiated with 5 Gy X-ray irradiation.
Figure 2B:
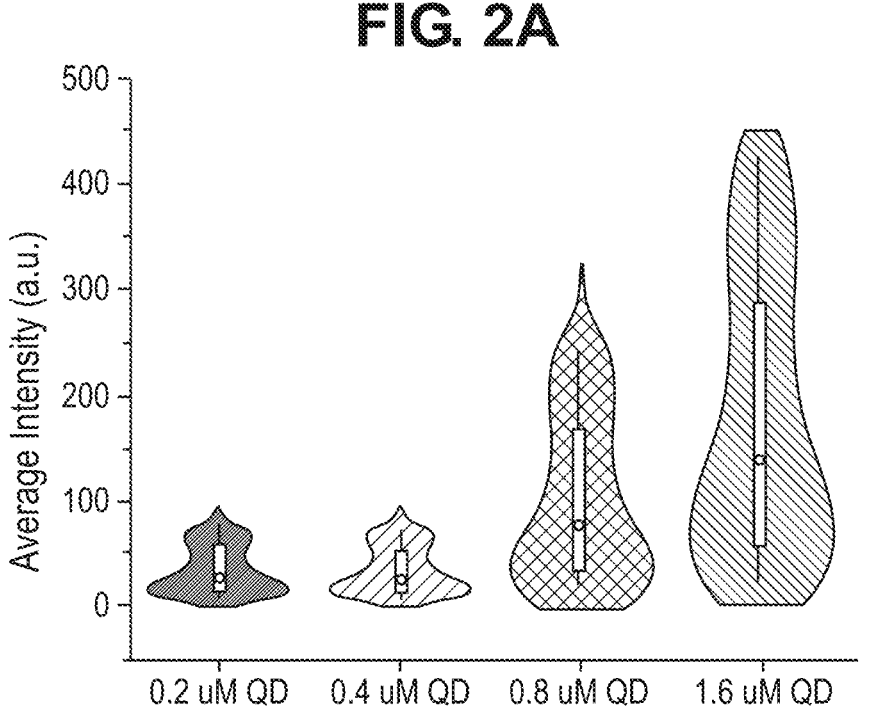
FIG. 2B is a violin plot of the data from FIG. 2A.

Referring to FIG. 2A, a chart is provided showing the average fluorescence intensity spectra for T98G cells inoculated with various concentrations of QD and irradiated with 5 Gy X-ray irradiation from an in-house CellRad radiation unit. Curve 200 represents data associated with 1.6 µM QD, curve 202 represents data associated with 0.8 µM QD, curve 204 represents data associated with 0.4 µM QD, and curve 206 represents data associated with 0.2 µM QD. The chart shows prominent increase in fluorescence intensity as QD concentration increased with exception of the fluorescence intensity between 0.2 µM and 0.4 µM QD, illustrating a mostly direct relationship between QD concentration and QD fluorescence. Referring to FIG. 2B, the peak, mean, and range fluorescence intensities are shown as a violin plot. Differences in the mean intensity were statistically significant with P<0.0001 between all concentrations except that there was no significant statistical difference in the mean intensity between 0.2 µM and 0.4 µM QD concentration.

Figure 3A:
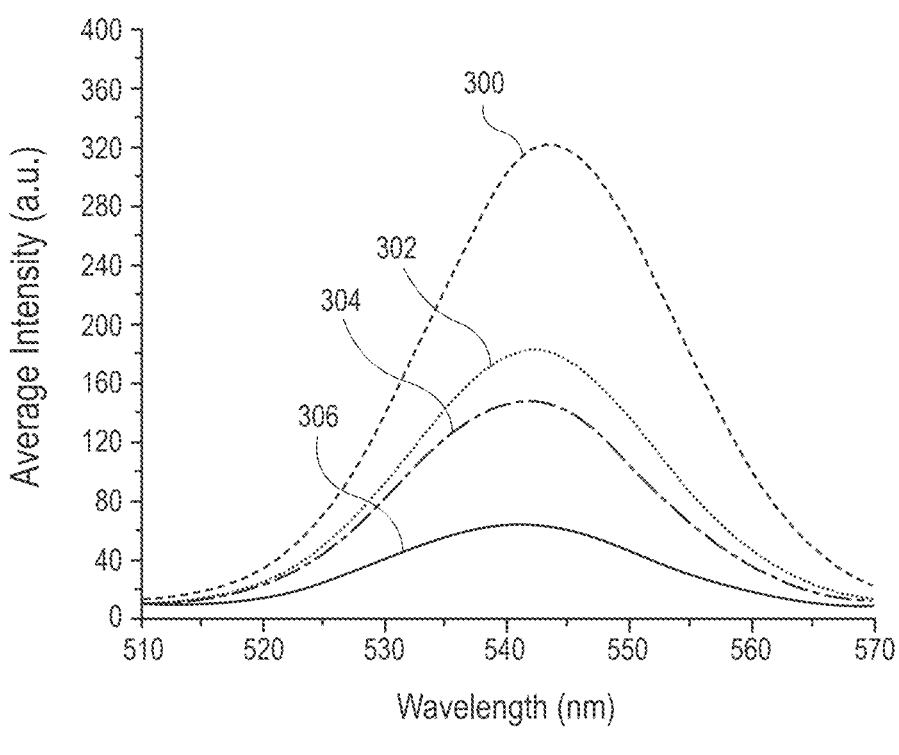
FIG. 3A is a chart of the average fluorescence intensity spectra for a line of glioblastoma cells inoculated with various concentrations of QD and irradiated with 20 Gy X-ray irradiation.
Figure 3B:
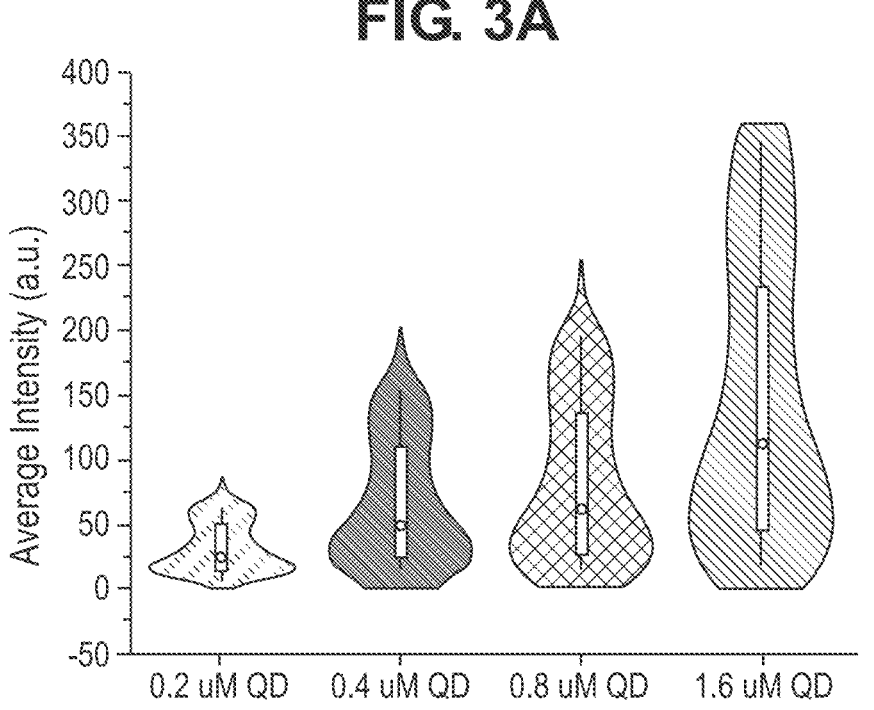
FIG. 3B is a violin plot of the data from FIG. 3A.

Similar observations were made with T98G cells inoculated with various QD concentrations that were subsequently irradiated with 20 Gy X-rays by the CellRad unit, with the associated chart provided in FIG. 3A. Curve 300 represents data associated with 1.6 µM QD, curve 302 represents data associated with 0.8 µM QD, curve 304 represents data associated with 0.4 µM QD, and curve 306 represents data associated with 0.2 µM QD. The data indicated that average fluorescence intensity increased with QD concentration. The greatest intensity was achieved with 1.6 µM concentration. The differences in mean intensity were statistically significant between all conditions. The peak, mean, and range average intensities are depicted in FIG. 3B. Differences in the mean intensity were statistically significant with $P<0.0001$ between all concentrations.

Figure 4A:
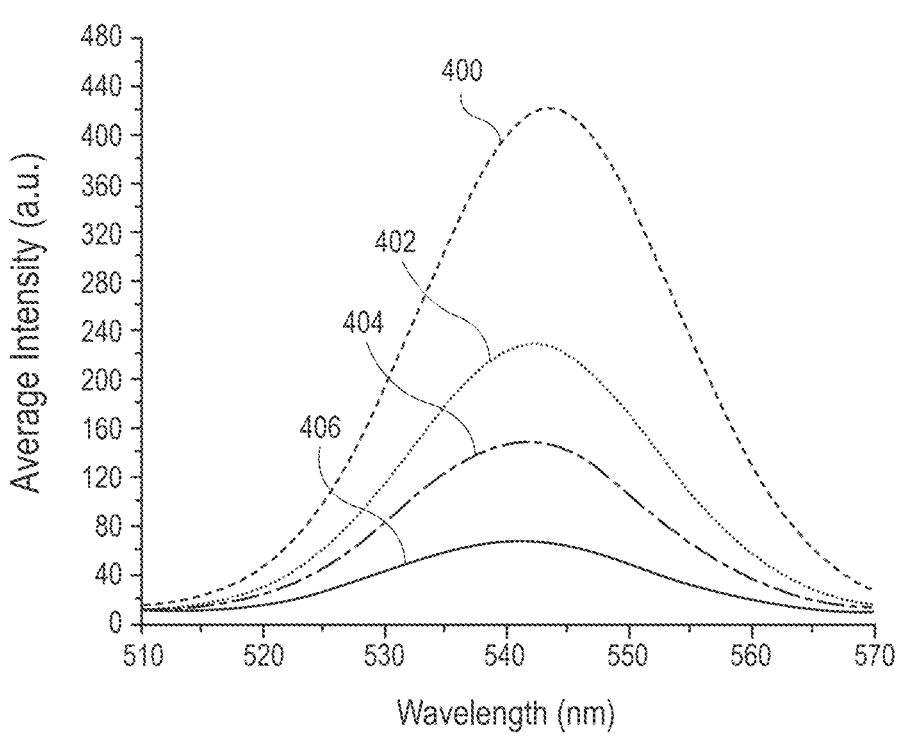
FIG. 4A is a chart of the average fluorescence intensity spectra for a line of glioblastoma cells inoculated with various concentrations of QD and irradiated with 5 Gy X-ray irradiation.
Figure 4B:
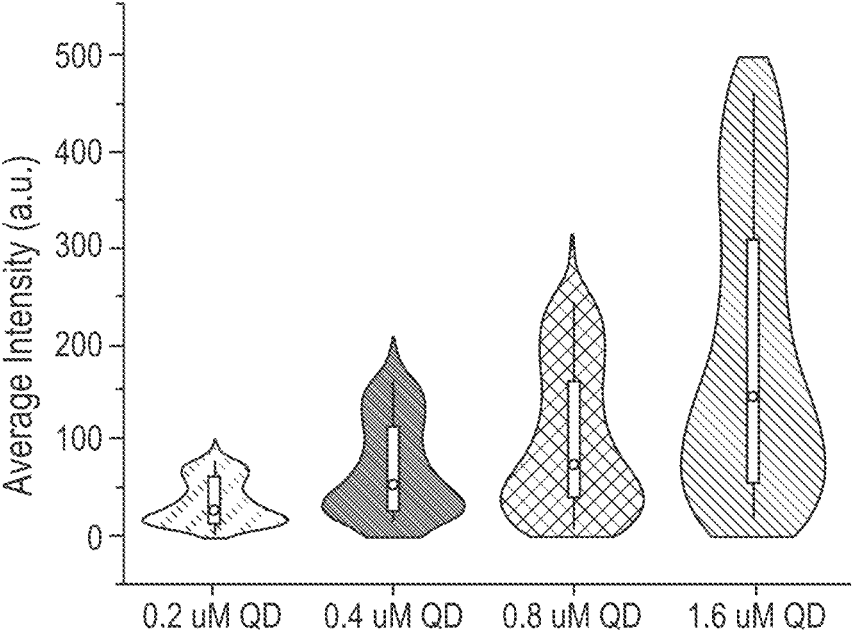
FIG. 4B is a violin plot of the data from FIG. 4A.

The fluorescence intensity dependency on QD concentration was also observed with the U87 cell line. Inoculated U87 cells at varying concentrations of QD and subject to 5 Gy X-ray irradiation expressed concentration dependency in fluorescence intensity as depicted in FIG. 4A. Curve 400 represents data associated with 1.6 µM QD, curve 402 represents data associated with 0.8 µM QD, curve 404 represents data associated with 0.4 µM QD, and curve 406 represents data associated with 0.2 µM QD. Of the tested conditions, the greatest average fluorescence intensity was observed with 1.6 µM QD and lowest with 0.2 µM QD. A violin plot of the data is shown in FIG. 4B, where there was no significant statistical difference in the mean between 0.2 µM and 0.4 µM QD as well as between 0.4 µM and 0.8 µM QD.

Figure 5A:
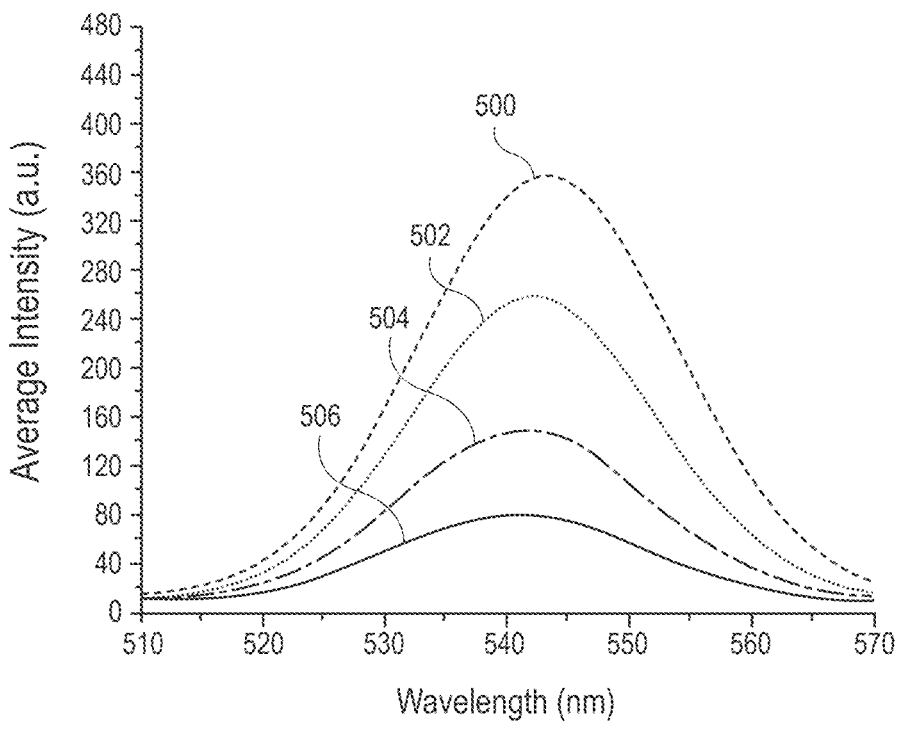
FIG. 5A is a chart of the average fluorescence intensity spectra for a line of glioblastoma cells inoculated with various concentrations of QD and irradiated with 20 Gy X-ray irradiation.
Figure 5B:
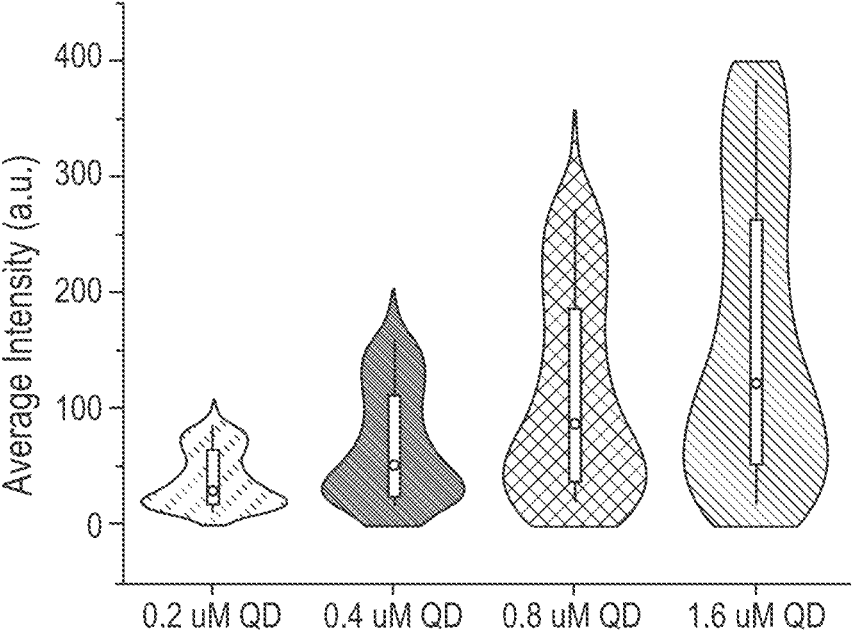
FIG. 5B is a violin plot of the data from FIG. 5A.

Similarly, U87 cells introduced to varying concentrations of QD and subsequently irradiated with 20 Gy X-rays indicated similar effect on fluorescence intensity. Greater concentrations of QD resulted in greater average fluorescence intensity as shown in FIG. 5A. Curve 500 represents data associated with 1.6 µM QD, curve 502 represents data associated with 0.8 µM QD, curve 504 represents data associated with 0.4 µM QD, and curve 506 represents data associated with 0.2 µM QD. One-way ANOVA analysis of the mean revealed statistically significant differences between all conditions, with FIG. 5B showing a violin plot of the peak, mean, and range of these conditions.

Graphene Quantum Dot Fluorescence Spectroscopy

Spectroscopic experiments with GQD were performed in triplet where the emission wavelength was determined to be 541.2 nm±0.2 nm with FWHM of 84 nm±2 nm. This was in agreement with the manufacturer's specification of 530 nm±10 nm emission and FWHM 80 nm, confirming their photophysical properties. Variations in these properties were attributed to the fixed variables of interest in the experimental conditions, particularly the modulation in fluorescence intensity due to the presence of ROS.

Figure 6A:
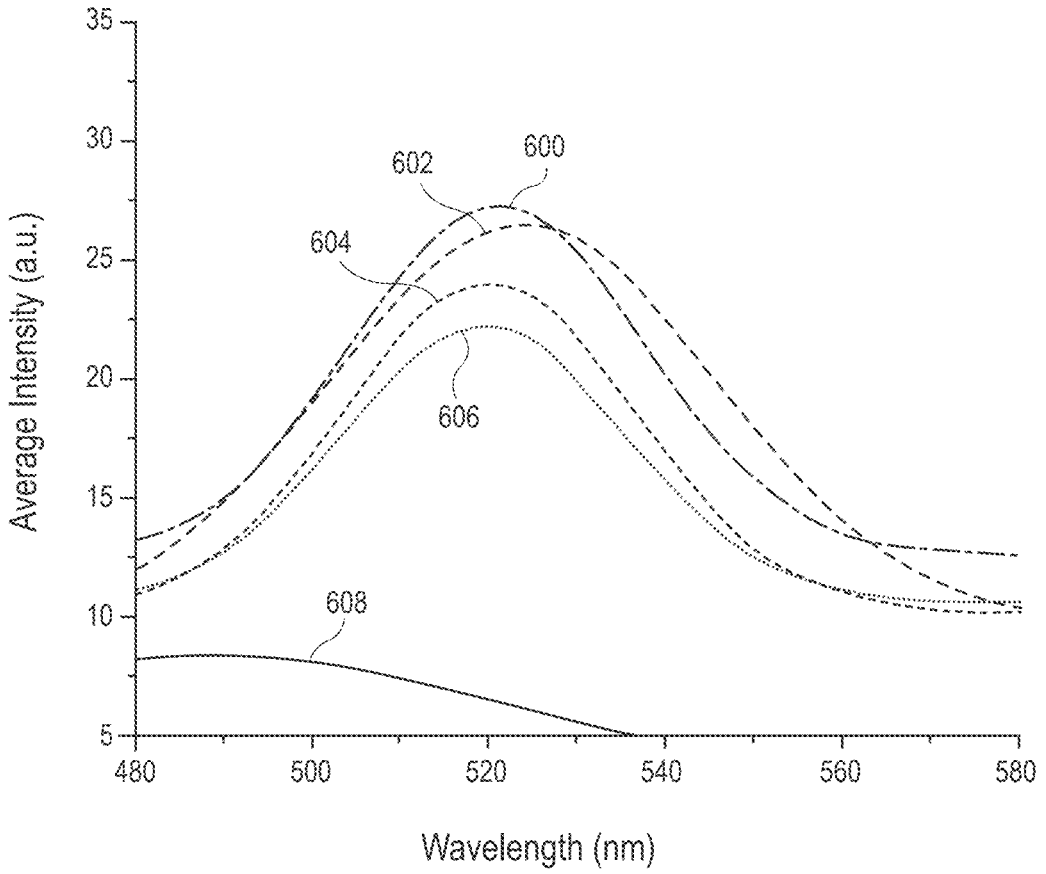
FIG. 6A is a chart of the average fluorescence intensity spectra for a line of glioblastoma cells inoculated with QD at one hour post-irradiation for various radiation doses.

Nanoparticle spectroscopy results for U87 glioblastoma cells inoculated with GQD at one hour post-irradiation are presented in FIG. 6A. Curve 600 represents data associated with cells treated and GQD with 5Gy, curve 602 represents data associated with cells treated with GQD and 20Gy, curve 604 represents data associated with cells treated with GQD with 5Gy, curve 606 represents data associated with cells treated with GQD, and curve 608 represents data associated with untreated cells. For these experiments, the radiation dose was varied instead of the concentration of NPs as with FIGS. 2A-5B. U87 cells without the presence of GQD provided a control for baseline spectra due to the presence of U87 and DMEM medium in all experimental conditions. This control condition showed little fluorescence intensity in each iteration around the 530 nm emission wavelength of GQD.

Figure 6B:
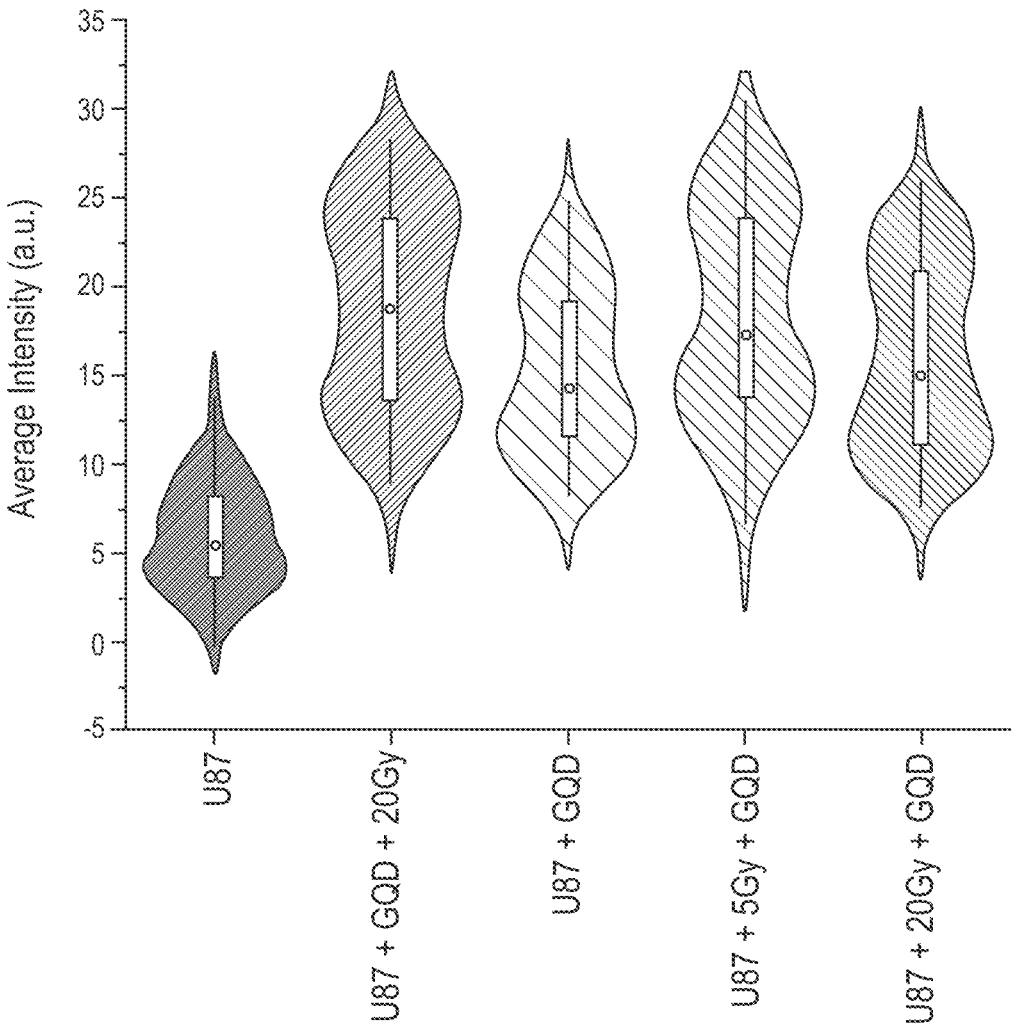
FIG. 6B is a violin plot of the data from FIG. 6A.

Modulation of the fluorescence intensity was present in all irradiated conditions and showed as enhancement of the fluorescence spectra. For the triplet, the enhancement was greatest with the 5 Gy dose showing a 10±10% enhancement in peak fluorescence intensity. This was statistically significant with $P<0.0001$. The calculated RPFI for 5 Gy was 400±70% for the triplet. U87 cells inoculated with GQD and received 20 Gy dose revealed lesser modulation in the fluorescence intensity emission at 2±4% across the triplet. This translated to a calculated RPFI of 1100±300%. Referring to FIG. 6B, a violin plot of the peak, mean, and range of these conditions is shown, where the optical enhancement in Condition 4 was statistically significant with $P<0.001$, but no significant statistical enhancement was observed in Condition 8.

Figure 7A:
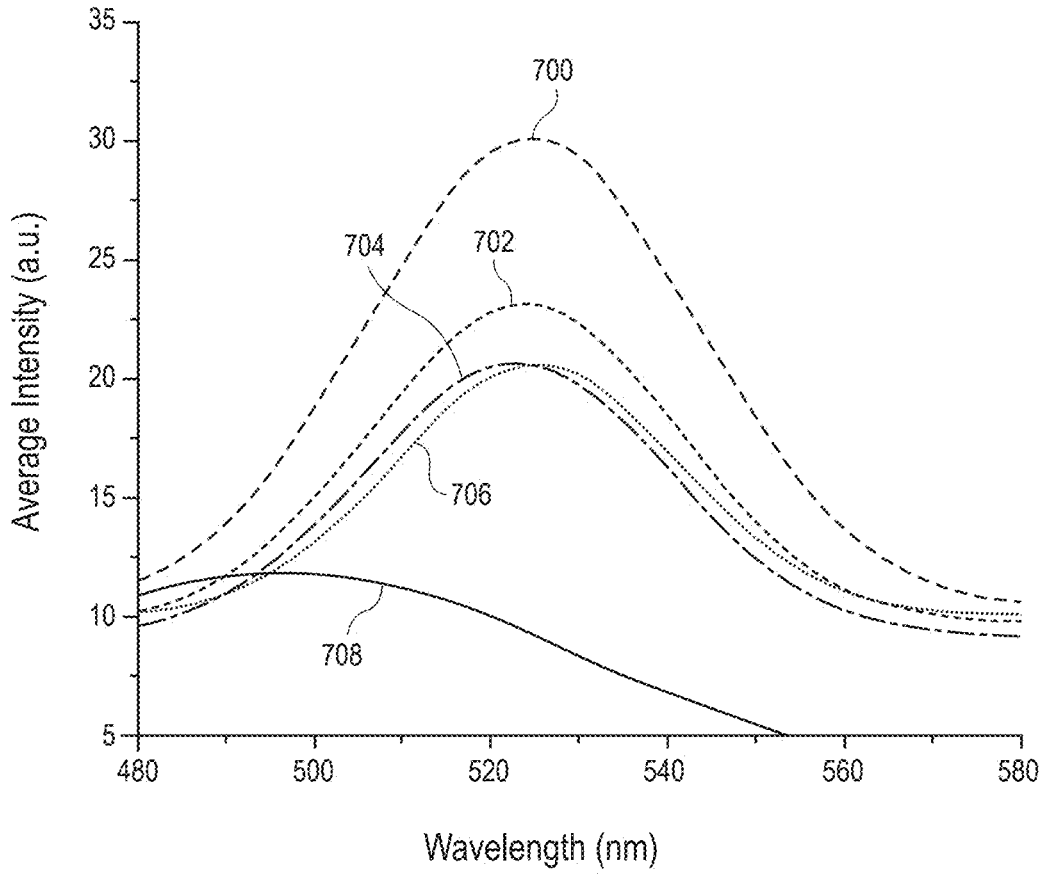
FIG. 7A is a chart of the average fluorescence intensity spectra for a line of glioblastoma cells inoculated with QD at one hour post-irradiation for various radiation doses.
Figure 7B:
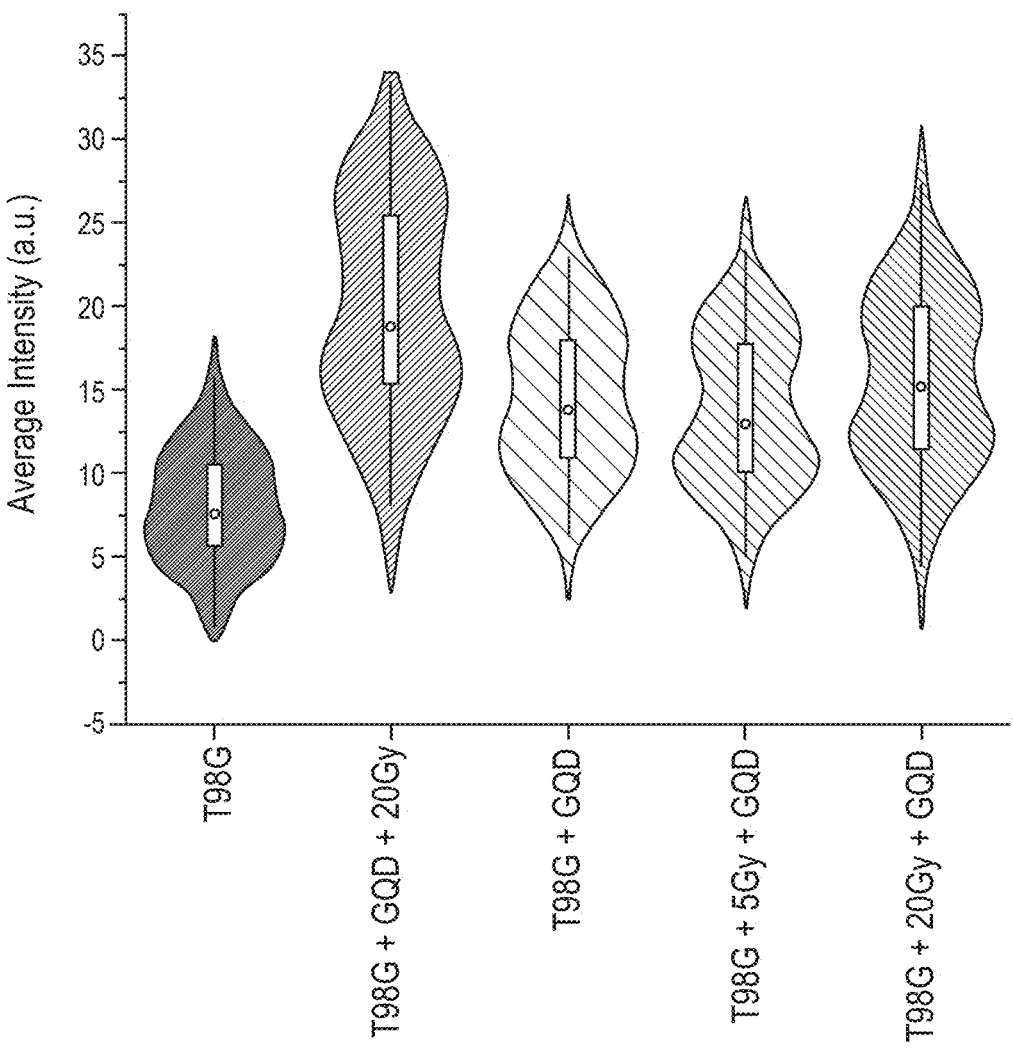
FIG. 7B is a violin plot of the data from FIG. 7A.

Nanoparticle spectroscopy results for T98G glioblastoma cells inoculated with GQD are shown in FIG. 7A. Curve 700 represents data associated with cells treated and GQD with 20Gy, curve 702 represents data associated with cells treated with GQD and 20Gy, curve 704 represents data associated with cells treated with GQD with 5Gy, curve 706 represents data associated with cells treated with GQD, and curve 708 represents data associated with untreated cells. Enhancement of the fluorescence intensity was observed in Conditions four and eight that received 20 Gy doses. Condition 4 had the greatest modulation in peak fluorescence intensity and was statistically significant with $P<0.0001$ as depicted in FIG. 7B that shows a violin plot of these conditions. The modulation was less pronounced in Condition 8 and was not statistically significant. Similarly, T98G cells inoculated with GQD that received 5 Gy dose displayed even less modulation in the fluorescence intensity emission. The fluctuating modulation in fluorescence emission intensity was consistent throughout the triplet. This translated to a −1±2% decrease in intensity at 5 Gy and 11±8% enhancement at 20 Gy across the three iterations of the experiment. The calculated RPFI was 2000±400% and 1800±700% for 5 Gy and 20 Gy respectively.

Graphene Quantum Dot Cell Survival Curves

Figure 8:
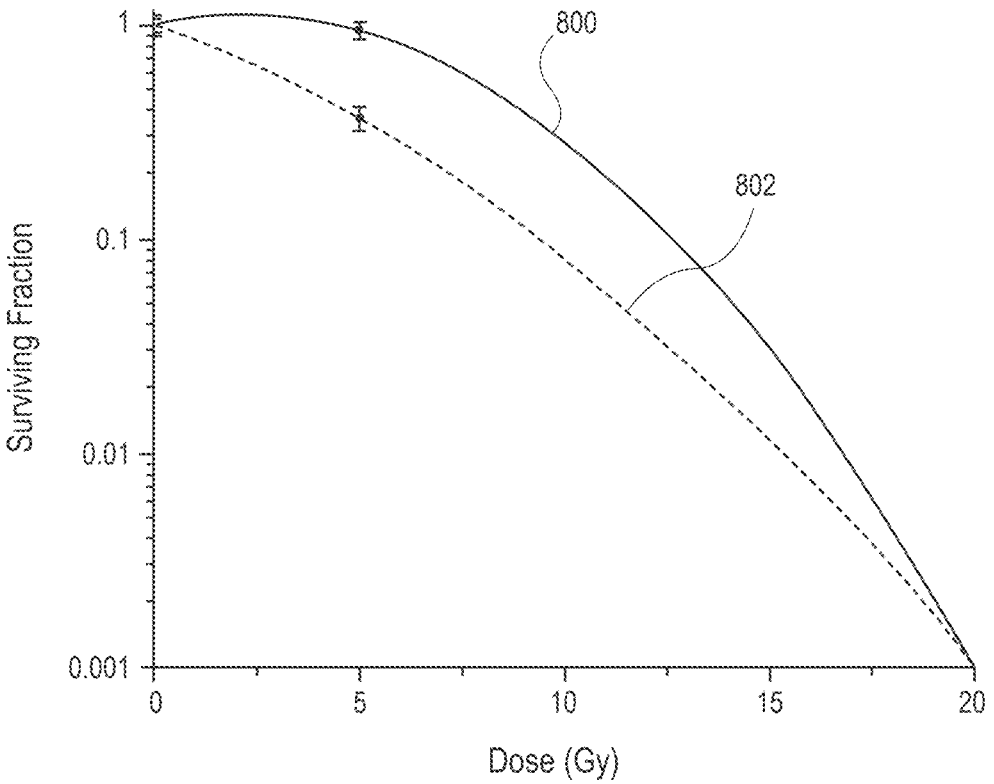
FIG. 8 is a chart of cell survival curves for a line of glioblastoma cells derived from clonogenic assays and treated at various radiation doses.

Clonogenic assay experiments with graphene quantum dots (GQD) were performed as outlined earlier. Cell survival curves for T98G cells treated at 0 Gy, 5 Gy, and 20 Gy derived from clonogenic assays are illustrated in FIG. 8 below. Curve 800 represents data associated with untreated cells and curve 802 represents data associated with cells treated with GQD. The survival curve for T98G cells that were not treated with nanoparticles (curve 800) displays a shoulder-like appearance as expected for low linear energy transfer (LET) X-ray irradiation. The survival curve for T98G cells treated with GQD (curve 802) displays much less of a shoulder. This indicates a much lower cell survival for cells irradiated with GQD. A linear quadratic model of the data revealed a much greater $\alpha/\beta$ ratio for T98G cells treated with GQD before irradiation ($\alpha/\beta$ ratio for T98G=4.5±0.9 Gy; $\alpha/\beta$ ratio for T98G with GQD=15±4 Gy).

ECIS Analysis of Graphene Quantum Dot Radiosensitization

Electric cell impedance sensing (ECIS) impedance analysis was employed to monitor cell migration, proliferation, and death. This was performed at 64 kHz where impedance is more influenced by cell-coverage to characterize migration and proliferation. The analysis was divided into three regions. The first region represents the initial migration and proliferation across electrodes once cells are placed in the incubator. This is characterized by a steady rise impedance where the rate is related to how quickly the cells migrate and proliferate. The second region begins when the migratory and growth patterns of the population of cells is greatly reduced marking a migratory endpoint as impedance plateaus. For a healthy population of cells, this happens when the population completely covers the surface. This is represented by a plateau in the impedance staying relatively constant. The final region occurs after the plateau or end-plateau point. The impedance decreases as cells die and lift from the surface of the electrodes.

There are several indications for radiosensitization for irradiated conditions inoculated with GQD. A first indication includes decreased rates of migration and proliferation in the first region represented by a slower increase in impedance measurements. The second indication includes the period of time it takes for the cell death to begin in the second region once reaching a plateau. This is represented by the duration of the plateau that ends when cells begin to die and lift. The third occurs in the final region describing the rate at which cells die and lift from the surface. Sharper decreases in impedance measurements indicate higher rates of cell death.

Figure 9A:
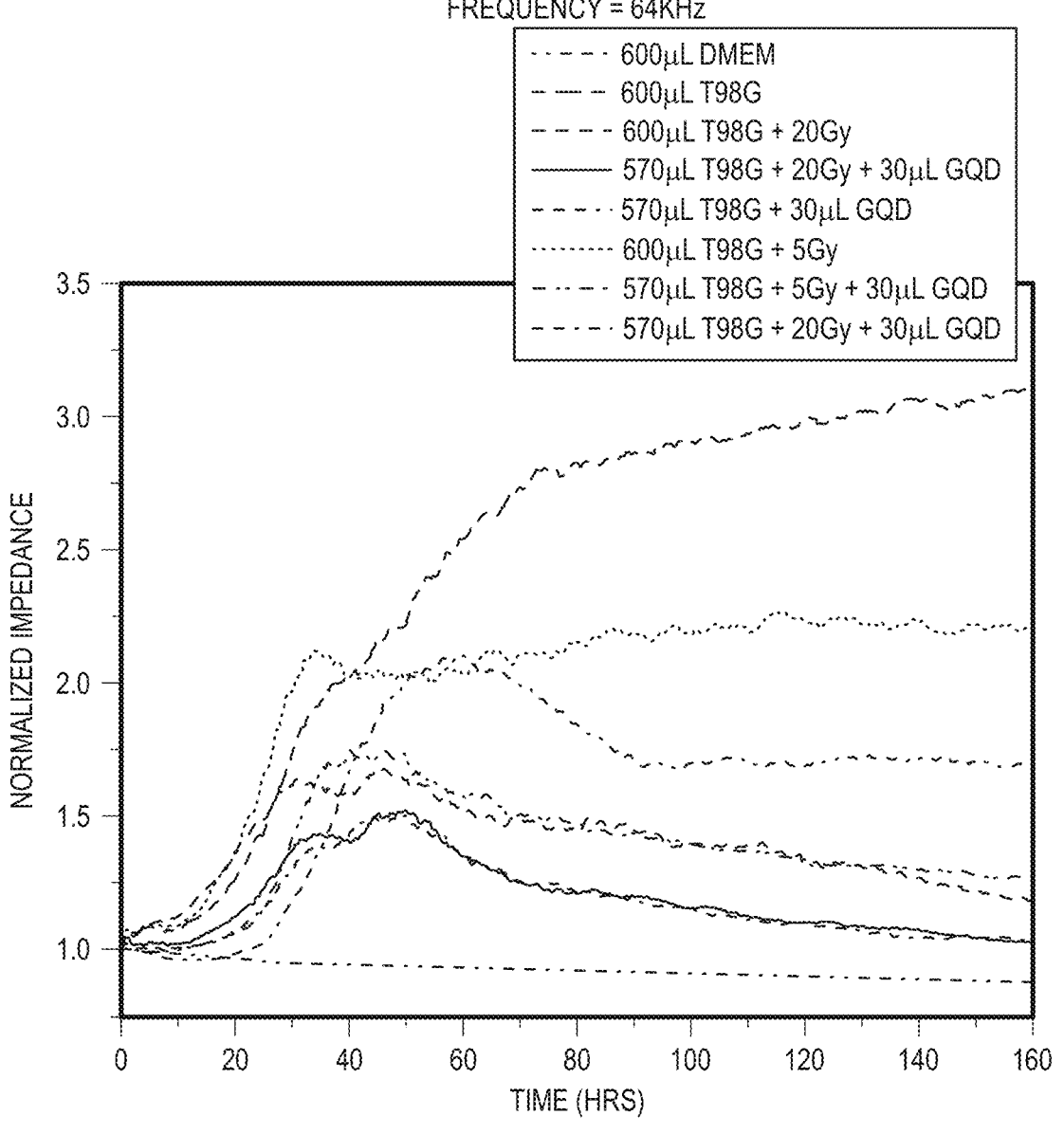
FIG. 9A is a chart of impedance monitoring of a line of glioblastoma cells treated according to various radiation doses with and without the presence of graphene QD.
Figure 9B:
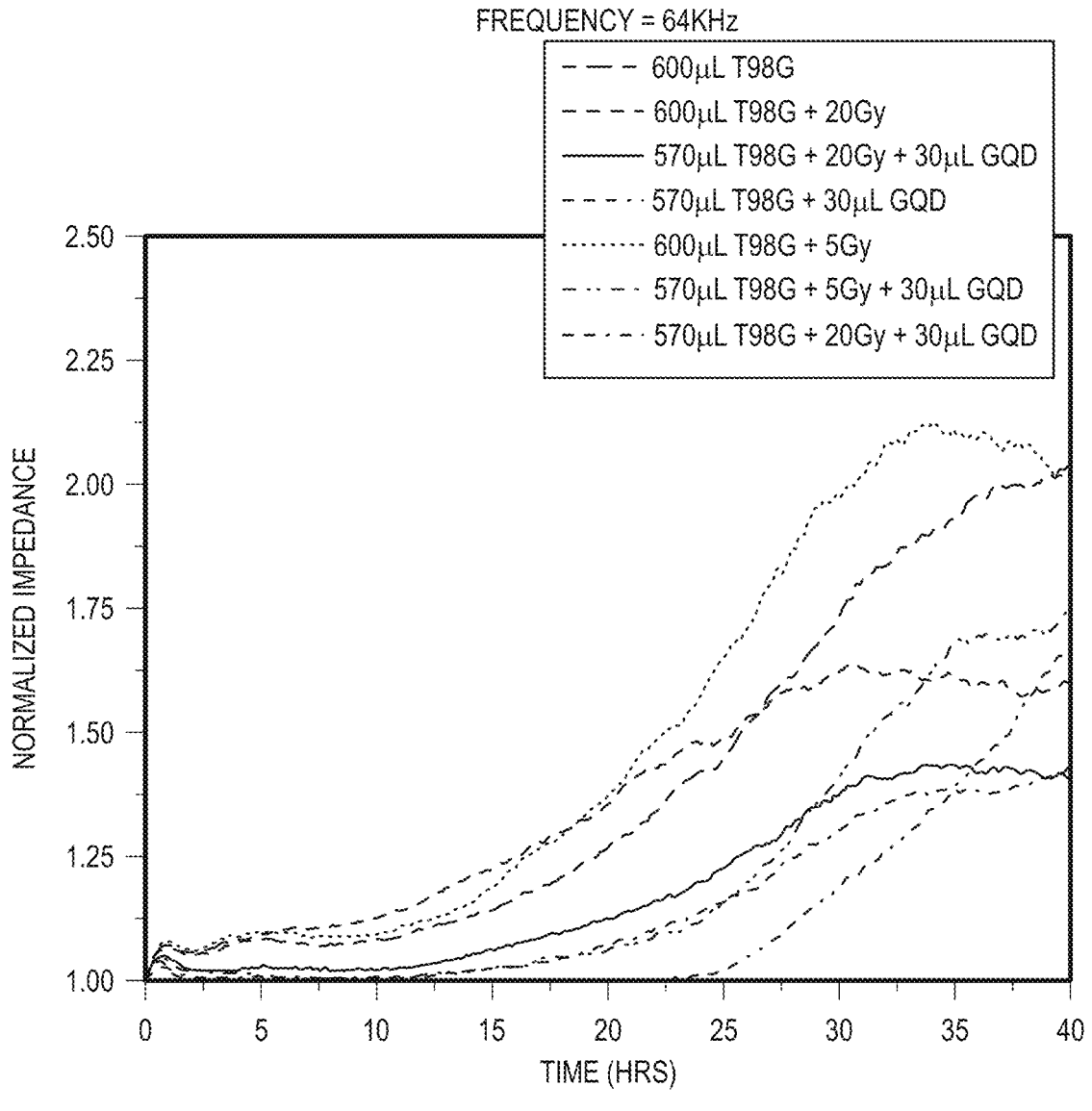
FIG. 9B is a first region of the chart shown in FIG. 9A.

Referring to FIGS. 9A and 9B, impedance monitoring of T98G inoculated with GQD is shown for 140 hour and 40 hour durations, respectively. The impedance for the control condition curve (e.g., containing only DMEM medium) stays relatively constant throughout the monitoring period confirming that there was no contamination and electronics were performing correctly. Compared to untreated T98G cells, cells treated with 5 Gy and cells treated with 20 Gy both expressed enhanced migration and proliferation. This illustrates an example where radiation elevates migratory patterns that can result in metastasis. A similar relationship was seen in the T98G cells inoculated with GQD that received 20 Gy dose. Untreated T98G cells and T98G cells that received 20 Gy dose had a much steeper rise in impedance in the first region (e.g., shown in FIG. 9B). This suggests that cells inoculated with GQD had decreased migration and proliferation comparatively. The trends shown in FIGS. 9A and 9B were also seen in the second and third replicates of the study.

An example of GQD radiosensitization is shown in FIGS. 9A and 9B with respect to T98G cells inoculated with GQD that received 5 Gy. In particular, T98G cells inoculated with GQD that received 5 Gy had a slower rise in impedance in the first region compared to both untreated T98G cells and T98G cells that received 5 Gy (but not inoculated with GQD). FIG. 9B further depicts decreased migration and proliferation for T98G cells inoculated with GQD that received 5 Gy. Additionally, untreated T98G cells and the T98G cells that received 5 Gy maintained their plateau region once reaching it. This indicates that the cells reached confluency and maintained a living layer of cells throughout the duration of the study. However, the T98G cells inoculated with GQD that received 5 Gy impedance began decreasing shortly after reaching the plateau. This suggests cells began to die and lift around 45 hrs into the study, a shorter timeframe as compared to T98G cells that were not inoculated with GQD.

Carbon Quantum Dot Fluorescence Spectroscopy at Clinical MV Energy

An experiment using a Siemens Oncor LINAC was performed using Jurkat, a radiosensitive leukemic cell line, where optical modulation of CQD fluorescence intensity indicates presence of ROS. The experiment was performed to investigate the functionality of CQD to enhance the production of ROS during radiation therapy using a clinical external beam radiation therapy machine, where this effect, in turn, radiosensitizes cancer cells.

Figure 10:
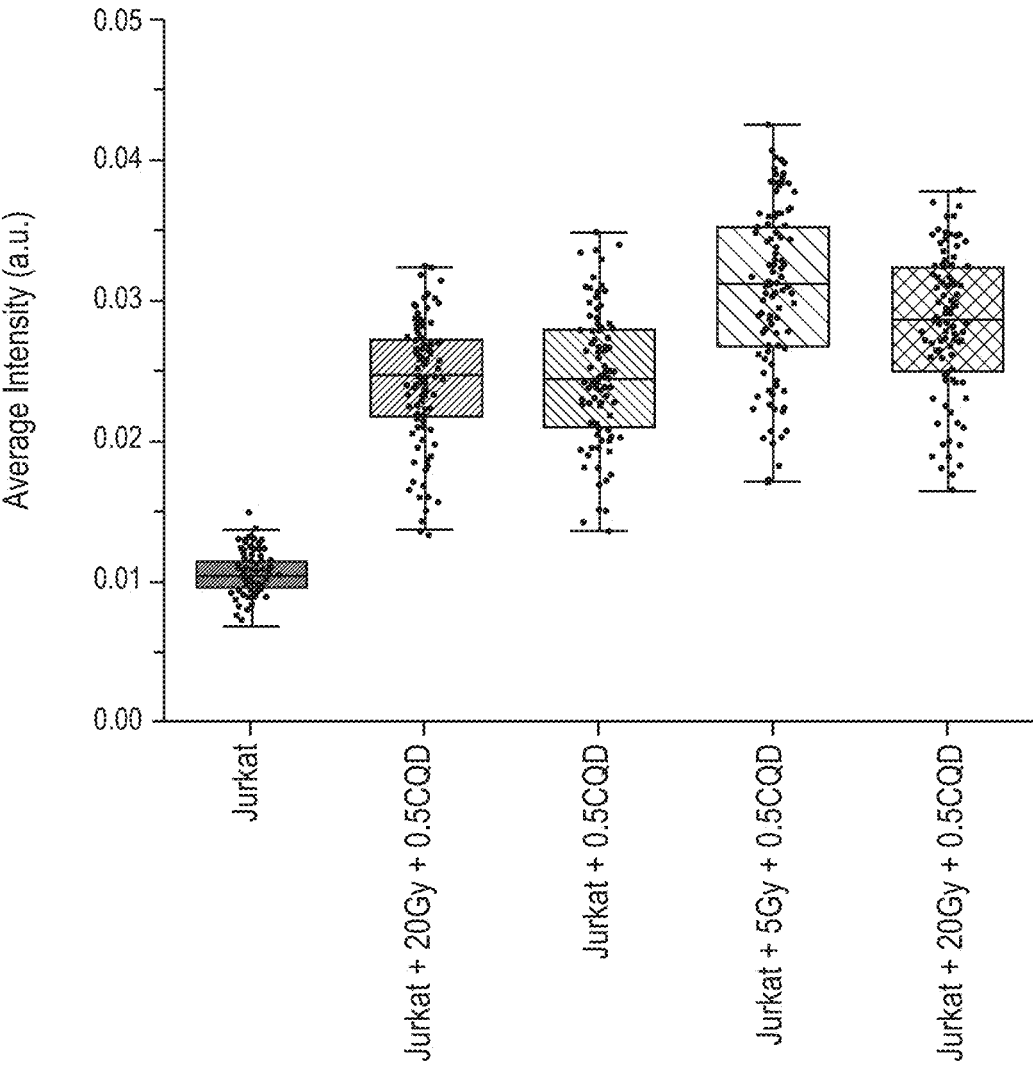
FIG. 10 is a boxplot of average fluorescence intensity spectra for a line of leukemia cells treated according to various radiation doses with and without the presence of carbon QD.

Referring to FIG. 10, a boxplot is provided that shows the fluorescence spectra of Jurkat cells inoculated with CQD, where the mean fluorescence intensity was used since the fluorescence emission of CQD extends from 450 to 550 nm. In particular, a 409.16% enhancement in the mean of the fluorescence spectra was observed in Jurkat cells inoculated with CQD that received 5 Gy compared to Jurkat cells inoculated with CQD without irradiation. The enhancement was statistically significant with $P<0.0001$. A 4.42% enhancement was also observed in condition eight composed of Jurkat cells inoculated with CQD that received 20 Gy irradiation compared to Jurkat cells inoculated with CQD without irradiation. This was statistically significant with $P<0.0001$. However, an observed 6.50% decrease in mean fluorescence intensity was appreciated in condition four composed of Jurkat cells inoculated with CQD that received 20 Gy and was not statistically significant.

CONCLUSION

Although the subject matter has been described in language specific to structural features and/or process operations, it is to be understood that the subject matter defined in the appended claims is not necessarily limited to the specific features or acts described above. Rather, the specific features and acts described above are disclosed as example forms of implementing the claims.

The invention claimed is:

1. A method for radiation therapy treatment of cancer cells, the method comprising:
   preparing a radiosensitizer fluid, the radiosensitizer fluid including a plurality of biocompatible quantum dots;
   introducing the radiosensitizer fluid to cancer cells;
   irradiating the cancer cells with the radiosensitizer fluid to promote generation of reactive oxygen species and inhibit radiation-induced enhancement of cell-migration; and
   measuring cell migration of the cancer cells, via electric cell impedance sensing (ECIS), following irradiation.

2. The method of claim 1, wherein the plurality of biocompatible quantum dots includes graphene quantum dots.

3. The method of claim 1, wherein the plurality of biocompatible quantum dots includes carbon quantum dots.

4. The method of claim 1, wherein the plurality of biocompatible quantum dots includes functionalized core/shell quantum dots.

5. The method of claim 4, wherein the functionalized core/shell quantum dots include quantum dots have a PEGy-lated CdSe core and a ZnS shell.

6. The method of claim 1, wherein the cancer cells include radioresistant cancer cells.

7. The method of claim 1, wherein the cancer cells include glioblastoma cells.

8. The method of claim 1, wherein the cancer cells include leukemia cells.

9. The method of claim 1, further comprising:
   measuring reactive oxygen species following irradiation.

10. The method of claim 1, further comprising:
   measuring cell survival of the cancer cells following irradiation.

11. A method for radiation therapy treatment of cancer cells, the method comprising:
   preparing a radiosensitizer fluid, the radiosensitizer fluid including a plurality of biocompatible quantum dots;
   introducing the radiosensitizer fluid to cancer cells;

irradiating the cancer cells with the radiosensitizer fluid to promote generation of reactive oxygen species and inhibit radiation-induced enhancement of cell-migration; and measuring cell migration of the cancer cells following irradiation.

12. A method for radiation therapy treatment of cancer cells, the method comprising:

preparing a radiosensitizer fluid, the radiosensitizer fluid including a plurality of biocompatible quantum dots present in an amount of at least 0.2 micromolar;

introducing the radiosensitizer fluid to human cancer cells;

irradiating the human cancer cells with the radiosensitizer fluid to promote generation of reactive oxygen species and inhibit radiation-induced enhancement of cell-migration; and measuring cell migration of the human cancer cells, via electric cell impedance sensing (ECIS), following irradiation.

13. The method of claim 12, wherein irradiating the human cancer cells with the radiosensitizer fluid to promote generation of reactive oxygen species and inhibit radiation-induced enhancement of cell-migration includes:

irradiating the human cancer cells with the radiosensitizer fluid to provide a dose of at least 5Gy to promote generation of reactive oxygen species and inhibit radiation-induced enhancement of cell-migration.

14. The method of claim 12, wherein the plurality of biocompatible quantum dots includes graphene quantum dots.

15. The method of claim 12, wherein the plurality of biocompatible quantum dots includes carbon quantum dots.

16. The method of claim 12, wherein the plurality of biocompatible quantum dots includes functionalized core/shell quantum dots.

17. The method of claim 16, wherein the functionalized core/shell quantum dots include quantum dots have a PEGylated CdSe core and a ZnS shell.

18. The method of claim 12, wherein the cancer cells include radioresistant cancer cells.

19. The method of claim 12, wherein the human cancer cells include glioblastoma cells.

20. The method of claim 12, wherein the human cancer cells include leukemia cells.

*     *     *     *     *